US010568490B2

(12) United States Patent
Dejima

(10) Patent No.: US 10,568,490 B2
(45) Date of Patent: Feb. 25, 2020

(54) SURGICAL APPARATUS FOR ENDOSCOPE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 401 days.

(21) Appl. No.: 15/470,911

(22) Filed: Mar. 28, 2017

(65) Prior Publication Data

US 2017/0196437 A1 Jul. 13, 2017

Related U.S. Application Data

(63) Continuation of application No. PCT/JP2015/077584, filed on Sep. 29, 2015.

(Continued)

(51) Int. Cl.
*A61B 1/00* (2006.01)
*A61B 17/34* (2006.01)
(Continued)

(52) U.S. Cl.
CPC ...... *A61B 1/00135* (2013.01); *A61B 1/00006* (2013.01); *A61B 1/00039* (2013.01);
(Continued)

(58) Field of Classification Search
CPC ............ A61B 1/00006; A61B 1/00039; A61B 1/00128; A61B 1/00133; A61B 1/00154;
(Continued)

(56) References Cited

U.S. PATENT DOCUMENTS 5,836,869 A 11/1998 Kudo et al.
6,221,007 B1 * 4/2001 Green ................ A61B 1/00052
600/104

(Continued)

FOREIGN PATENT DOCUMENTS

EP 1854420 11/2007
EP 1935354 6/2008
(Continued)

OTHER PUBLICATIONS

"International Preliminary Report on Patentability (Form PCT/IPEA/409)", published on Nov. 30, 2016, with English translation thereof, pp. 1-11.

(Continued)

*Primary Examiner* — John P Leubecker
*Assistant Examiner* — Shankar Raj Ghimire
(74) *Attorney, Agent, or Firm* — JCIPRNET

(57) ABSTRACT

Provided is a surgical apparatus for an endoscope with which an operator can change, as desired, the size of an image of a site to be observed that appears in an endoscopic image obtained by an endoscope or the size of the range of the site to be observed. An image processing unit (zooming means) of a processor device changes a zoom magnification factor of an endoscopic image from an endoscope through electronic zooming on the basis of the operation of a foot switch. In the non-sensing region of the slider, the activation and deactivation of the zooming operation by the foot switch are switched according to a relative position of a distal end of the endoscope with respect to a distal end of the treatment tool.

7 Claims, 19 Drawing Sheets

Related U.S. Application Data

(60) Provisional application No. 62/057,516, filed on Sep. 30, 2014.

(51) Int. Cl.
*A61B 1/018* (2006.01)
*A61B 1/313* (2006.01)
*A61B 90/00* (2016.01)

(52) U.S. Cl.
CPC ...... *A61B 1/00128* (2013.01); *A61B 1/00133* (2013.01); *A61B 1/00154* (2013.01); *A61B 1/00188* (2013.01); *A61B 1/018* (2013.01); *A61B 1/3132* (2013.01); *A61B 17/3415* (2013.01); *A61B 17/3421* (2013.01); *A61B 90/361* (2016.02); *A61B 2017/3441* (2013.01); *A61B 2017/3445* (2013.01); *A61B 2017/3447* (2013.01); *A61B 2017/3466* (2013.01); *A61B 2090/0811* (2016.02)

(58) Field of Classification Search
CPC ... A61B 1/00188; A61B 1/018; A61B 1/3132; A61B 17/3415; A61B 17/3421; A61B 2090/0811; A61B 90/361; A61B 2017/3445; A61B 2017/3447; A61B 2017/3466
See application file for complete search history.

(56) References Cited

U.S. PATENT DOCUMENTS

| | | | |
|---|---|---|---|
| 7,841,980 B2 | 11/2010 | Minosawa et al. | |
| 2004/0130651 A1* | 7/2004 | Wakashiro | A61B 1/00188 348/349 |
| 2005/0119525 A1* | 6/2005 | Takemoto | A61B 1/00154 600/114 |
| 2005/0267335 A1* | 12/2005 | Okada | A61B 1/0014 600/173 |
| 2007/0265502 A1* | 11/2007 | Minosawa | A61B 1/00177 600/173 |
| 2008/0051631 A1* | 2/2008 | Dejima | A61B 1/0052 600/114 |
| 2010/0016659 A1* | 1/2010 | Weitzner | A61B 1/00073 600/104 |
| 2012/0162402 A1* | 6/2012 | Amano | A61B 1/00096 348/65 |
| 2012/0226101 A1* | 9/2012 | Tinkham | A61B 1/00066 600/106 |
| 2015/0080650 A1 | 3/2015 | Dejima et al. | |
| 2015/0198797 A1* | 7/2015 | Andre | A61B 5/7425 348/80 |
| 2016/0045100 A1* | 2/2016 | Eto | A61B 1/00087 600/106 |

FOREIGN PATENT DOCUMENTS

| | | | |
|---|---|---|---|
| EP | 2979619 | 2/2016 | |
| JP | 2004-041778 | 2/2004 | |
| JP | 2007-301378 | 11/2007 | |
| WO | 2013176167 | 11/2013 | |
| WO | WO-2013176167 A1 * | 11/2013 | ...... A61B 1/00135 |

OTHER PUBLICATIONS

"Search Report of European Counterpart Application," dated Aug. 30, 2017, p. 1-p. 12, in which the listed references were cited.

* cited by examiner

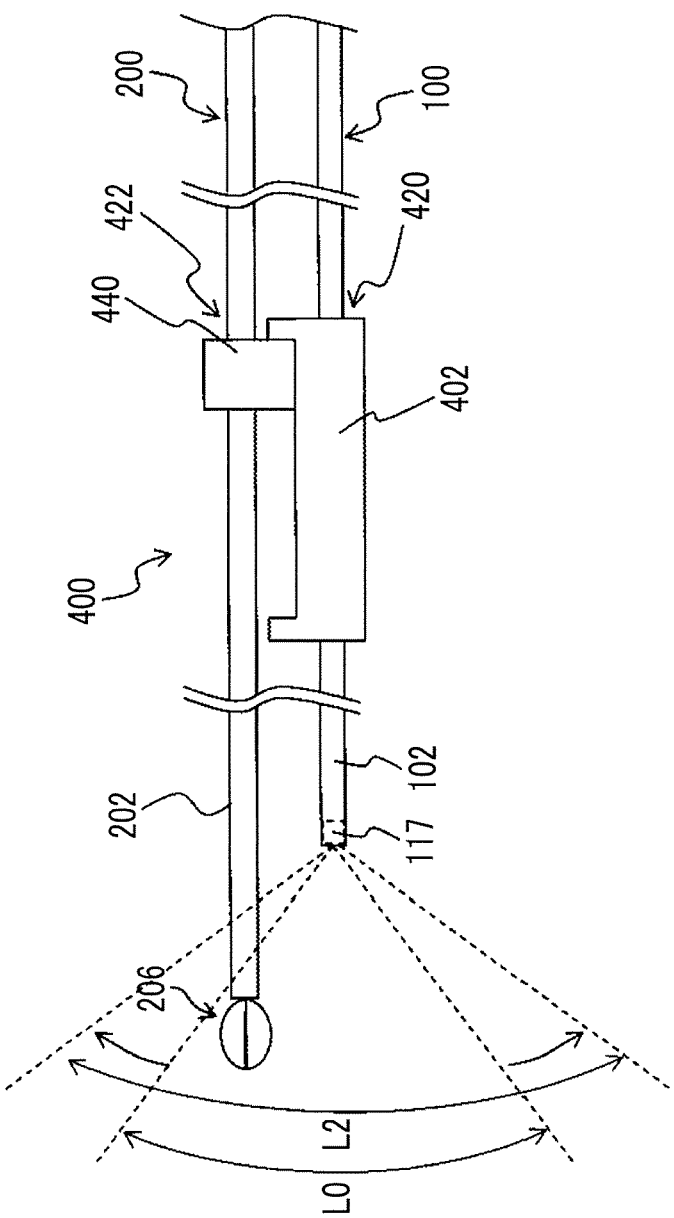

SURGICAL APPARATUS FOR ENDOSCOPE

CROSS-REFERENCE TO RELATED APPLICATIONS

This application is a Continuation of PCT International Application No. PCT/JP2015/077584 filed on Sep. 29, 2015, which claims priority under 35 U.S.C. § 119(a) to U.S. Provisional Application No. 62/057,516 filed on Sep. 30, 2014. Each of the above applications is hereby expressly incorporated by reference, in their entirety, into the present application.

BACKGROUND OF THE INVENTION

1. Field of the Invention

The present invention relates to a surgical apparatus for an endoscope, and particularly, relates to a surgical apparatus for an endoscope that can operate an endoscope and a treatment tool inserted through two insertion passages provided in an outer tube in an interlocking manner.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, is widely performed. In the endoscopic surgery, a plurality of holes are made in a patient's body wall, an endoscope is inserted into a body cavity from one hole of them, and a treatment tool is inserted into the body cavity from another hole. Then, treatment of a living body tissue is performed with the treatment tool while observing the living body tissue within the body cavity with the endoscope.

Generally, in the endoscopic surgery, one or a plurality of treatment tools are used simultaneously with the endoscope. Therefore, since it is difficult for one operator to simultaneously operate the endoscope and the plurality of treatment tools, for example, a task where the operator operates treatment tools using both hands while making an assistant called an endoscopic technician operate the endoscope is normally performed.

In this way, in the endoscopic surgery, it is general that the operator's hands are bound by the operation of the treatment tool, and the operation of the endoscope is performed by the assistant. Therefore, in a case where the observation position of the endoscope is changed, the operator should serially give instructions to the assistant. Hence, the task of correctly directing the orientation of the endoscope to a direction desired by the operator is difficult, and stress is likely to be imposed on the operator. Additionally, since the assistant performs an operation after the operator issues an instruction, there is a tendency that surgery time is likely to be prolonged. Additionally, the assistant should operate the endoscope so as not to interfere with an operator's procedure, and the operation is likely to become complicated.

In contrast, the applicant of the present application suggests a technique in which an endoscope and a treatment tool are combined together by an outer tube, and if the treatment tool is moved forward and backward, the endoscope is also moved forward and backward in an interlocking manner with this movement of the treatment tool (refer to WO2013/176167A). Specifically, the outer tube that guides an insertion part of the endoscope and an insertion part of the treatment tool into a body cavity includes a tubular outer tube body that is inserted in a state where the insertion part of the endoscope and the insertion part of the treatment tool are made to be parallel to each other. An interlocking member that is movable forward and backward in an axial direction and has an endoscope-coupling part and a treatment tool-coupling part is provided inside the outer tube body. The insertion part of the endoscope and the insertion part of the treatment tool are held by the respective coupling parts of the interlocking member in a state where the insertion parts are made to be parallel to each other. If the insertion part of the treatment tool is moved in the axial direction, the insertion part of the endoscope also moves in the axial direction in an interlocking manner with this movement. Accordingly, the number of the holes made in the patient's body wall can be reduced, the invasion to the patient can be suppressed, and the visual field of the endoscope can be easily changed while an operator operates the treatment tool without asking for an assistant's help.

Additionally, in WO2013/176167A, the applicant of the present application suggests a configuration in which play is provided for the coupling between the endoscope and the treatment tool while the interlocking member is kept from interlocking with a small amplitude of movement of the endoscope or the treatment tool.

SUMMARY OF THE INVENTION

Meanwhile, in the technique that the applicant of the present application has suggested through WO2013/176167A, a relative position of a distal end of the endoscope with respect to a distal end of a treatment tool varies depending on the play of the interlocking member with respect to the forward and backward movement of the endoscope or the treatment tool. Along with this, the size of an image of a site to be observed, such as a distal end site of the treatment tool or a lesioned site, that appears in an endoscopic image acquired by an observation part of the endoscope, or the size of the range of a site to be observed that appears in the endoscopic image varies. It can be assumed that such a change is not desired depending on an operator.

Additionally, it is desired that an operator can change the size of the image of the site to be observed that appears in the endoscopic image or the size of the range of the site to be observed depending on a situation.

The invention has been made in view of such circumstances, and an object thereof is to provide a surgical apparatus for an endoscope with which an operator can change, as desired, the size of an image of a site to be observed that appears in an endoscopic image obtained by an endoscope or the size of the range of the site to be observed.

In order to achieve the above object, a surgical apparatus for an endoscope according to an aspect of the invention is a surgical apparatus for an endoscope comprising an endoscope having an image pickup element disposed at a distal end thereof; a treatment tool having a treatment part at a distal end thereof; an outer tube that passes through a body wall and is inserted into a body cavity to guide the endoscope and the treatment tool into the body cavity; and a control device connected to the endoscope. The outer tube includes an outer tube body having a distal end, a base end, and a longitudinal axis, a first distal end opening and a second distal end opening provided at the distal end of the outer tube body, a first base end opening and a second base end opening provided at the base end of the outer tube body, an endoscope insertion passage that is provided along the longitudinal axis of the outer tube body, allows the first distal end opening and the first base end opening to communicate with each other therethrough, and allows the endoscope to be inserted therethrough so as to be movable forward and backward, a treatment tool insertion passage that is provided along the longitudinal axis of the outer tube body, allows the second distal end opening and the second base end opening to communicate with each other therethrough, and allows the treatment tool to be inserted therethrough so as to be movable forward and backward, and an interlocking member that has an endoscope-coupling part coupled to the endoscope inserted through the endoscope insertion passage, and a treatment tool-coupling part coupled to the treatment tool inserted through the treatment tool insertion passage and is movable forward and backward inside the outer tube body. When a relative position of the endoscope-coupling part with respect to the treatment tool-coupling part when the distal end of the endoscope approaches the distal end of the treatment tool most in a longitudinal axis direction of the outer tube body is defined as a first position, and when a relative position of the endoscope-coupling part with respect to the treatment tool-coupling part when the distal end of the endoscope is separated from the distal end of the treatment tool most in the longitudinal axis direction of the outer tube body is defined as a second position, the interlocking member has a non-sensing region where the relative position of the distal end of the endoscope with respect to the distal end of the treatment tool varies while the relative position of the endoscope-coupling part with respect to the treatment tool-coupling part varies between the first position and the second position, and a sensing region where the relative position of the distal end of the endoscope with respect to the distal end of the treatment tool does not vary with the relative position of the endoscope-coupling part with respect to the treatment tool-coupling part being the first position or the second position. The endoscope or the control device includes zooming means for changing a zoom magnification factor of an endoscopic image picked up by the image pickup element, and zoom operating means provided in the endoscope or the control device for operating the zooming means. The surgical apparatus for an endoscope further comprises detecting means for detecting the relative position of the distal end of the endoscope with respect to the distal end of the treatment tool in the longitudinal axis direction of the outer tube body; and switching means for switching between activation and deactivation of the operation of the zooming means by the zoom operating means, on the basis of a detection result of the detecting means.

According to the invention, by operating the zoom operating means to change the zoom magnification factor of the endoscopic image with the zooming means, the operator can change, as desired, the size of an image of a site to be observed that appears in the endoscopic image obtained by the endoscope or the size of the range of the site to be observed. Additionally, by providing the switching means that deactivates the operation of the zooming means on the basis of the relative position of the distal end of the endoscope with respect to the distal end of the treatment tool that is detected by the detecting means, the zoom operating means can be prevented from unintentionally being operated.

In the surgical apparatus for an endoscope according to the aspect of the invention, it is possible to adopt an aspect in which, when the relative position of the endoscope-coupling part with respect to the treatment tool-coupling part when the distal end of the endoscope approaches the distal end of the treatment tool most in the longitudinal axis direction of the outer tube body is defined as the first position, and when the relative position of the endoscope-coupling part with respect to the treatment tool-coupling part when the distal end of the endoscope is separated from the distal end of the treatment tool most in the longitudinal axis direction of the outer tube body is defined as the second position, the interlocking member changes the relative position of the endoscope-coupling part with respect to the treatment tool-coupling part between the first position and the second position, and the detecting means detects the relative position of the endoscope-coupling part with respect to the treatment tool-coupling part, thereby detecting the relative position of the distal end of the endoscope with respect to the distal end of the treatment tool.

This aspect is one form of the detecting means that detects the relative position of the distal end of the endoscope with respect to the distal end of the treatment tool in the longitudinal axis direction of the outer tube body. The detecting means can be simply realized, for example, by being installed in a coupling member.

In the surgical apparatus for an endoscope according to the aspect of the invention, it is possible to adopt an aspect in which the switching means activates the operation of the zooming means by the zoom operating means in a case where the relative position of the endoscope-coupling part with respect to the treatment tool-coupling part has a shorter distance from the second position than a distance from the first position, and deactivates the operation of the zooming means by the zoom operating means in a case where the relative position of the endoscope-coupling part with respect to the treatment tool-coupling part has a shorter distance from the first position than a distance from the second position.

According to this aspect, the zoom magnification factor of the endoscopic image can be changed by moving the treatment tool forward or moving the endoscope backward in the non-sensing region of the interlocking member, thereby performing the operation of the zooming means by the zoom operating means. Additionally, a state where the zoom magnification factor of the endoscopic image is not changed even if the operation of the zooming means by the zoom operating means is performed by moving the treatment tool backward or moving the endoscope forward is brought about.

In the surgical apparatus for an endoscope according to the aspect of the invention, it is possible to adopt an aspect in which the switching means activates the operation of the zooming means by the zoom operating means in a case where the relative position of the endoscope-coupling part with respect to the treatment tool-coupling part has a shorter distance from the first position than a distance from the second position, and deactivates the operation of the zooming means by the zoom operating means in a case where the relative position of the endoscope-coupling part with respect to the treatment tool-coupling part has a shorter distance from the second position than a distance from the first position.

According to this aspect, the zoom magnification factor of the endoscopic image can be changed by moving the treatment tool backward or moving the endoscope forward in the non-sensing region of the interlocking member, thereby performing the operation of the zooming means by the zoom operating means. Additionally, a state where the zoom magnification factor of the endoscopic image is not changed even if the operation of the zooming means by the zoom operating means is performed by moving the treatment tool forward or moving the endoscope backward is brought about.

In the surgical apparatus for an endoscope according to the aspect of the invention, it is possible to adopt an aspect in which the zooming means changes the zoom magnification factor through at least one of optical zooming or electronic zooming.

As in this aspect, the change of the zoom magnification factor of the endoscopic image may be performed by the optical zooming or may be performed by the electronic zooming.

In the surgical apparatus for an endoscope according to the aspect of the invention, it is possible to adopt an aspect in which the zoom operating means has a first operation switch that zooms in the endoscopic image, and a second operation switch that zooms out the endoscopic image.

In the surgical apparatus for an endoscope according to the aspect of the invention, it is possible to adopt an aspect in which the zooming means continuously changes the zoom magnification factor while the first operation switch or the second operation switch is continuously operated.

In the surgical apparatus for an endoscope according to the aspect of the invention, it is possible to adopt an aspect in which the zoom operating means is a foot switch.

According to this aspect, the zoom magnification factor of the endoscopic image can be changed without using a hand.

According to the invention, an operator can change, as desired, the size of the image of the site to be observed that appears in the endoscopic image obtained by the endoscope or the size of the range of the site to be observed.

BRIEF DESCRIPTION OF THE DRAWINGS

FIG. 21 is a view illustrating a state when the relative position of the endoscope-coupling part with respect to the treatment tool-coupling part is the first position, and is a view illustrating a state when zoom magnification factor is reduced.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
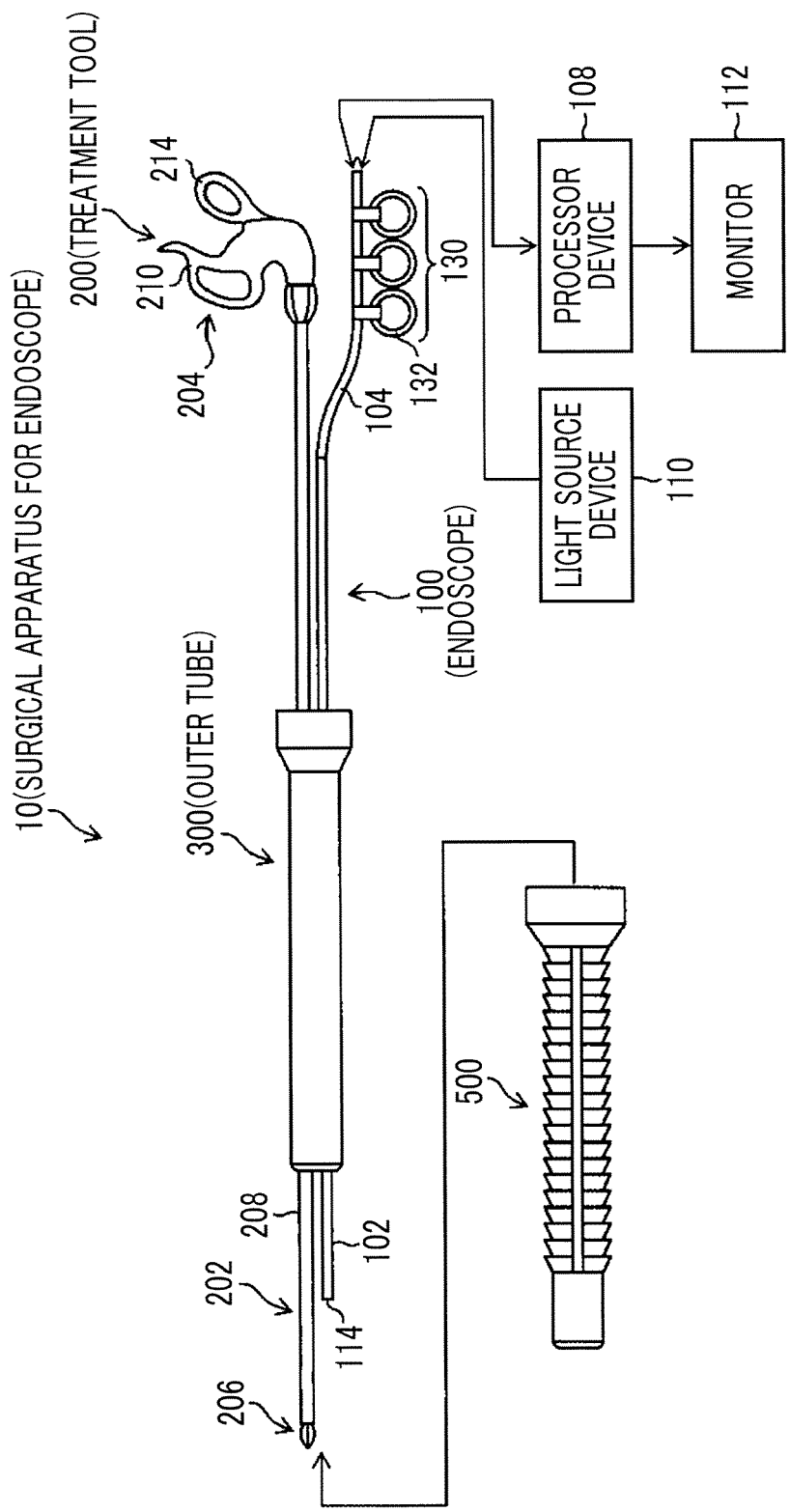
FIG. 1 is a schematic block diagram of a surgical apparatus for an endoscope according to the invention.

FIG. 1 is a schematic block diagram of a surgical apparatus for an endoscope according to the invention. As illustrated in FIG. 1, a surgical apparatus for an endoscope 10 includes an endoscope 100 that observes the inside of a patient's body cavity, a treatment tool 200 for examining or treating a diseased site within the patient's body cavity, an outer tube 300 that is inserted into a body wall and guides the endoscope 100 and the treatment tool 200 into the body cavity, and an exterior tube 500 fitted to the outer tube 300.

The endoscope 100 is, for example, a hard endoscope, such as a laparoscope, and includes an insertion part 102 (hereinafter referred to as "endoscope insertion part 102") that is inserted into a body cavity, and that has an outer peripheral part surrounded by an elongated hard tubular body, and a cable part 104 that is provided continuously with a base end side of the endoscope insertion part 102 and that has an outer peripheral part surrounded by an elongated flexible tubular body.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 that is a control device and a light source device 110 is detachably connected to the cable part via the connector. Additionally, the processor device 108 is connected to a monitor 112 via a cable.

Figure 2:
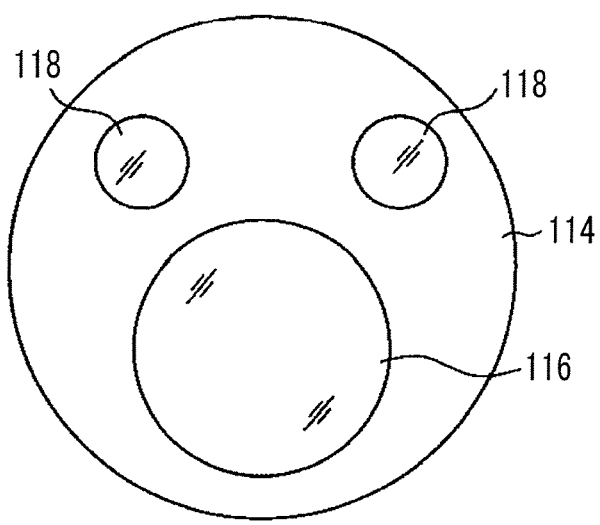
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and a solid image pickup element, such as a charge coupled device (CCD) image sensor or a complementary metal oxide semiconductor (CMOS) image sensor, which is disposed at an image pickup position of the objective lens, are disposed behind the observation window 116. A signal cable (not illustrated) connected to this solid image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pickup element, and is converted into electrical signals (image pickup signals), and the electrical signals are output to the processor device 108 via the signal cable and are converted into video signals. Then, the video signals are output to the monitor 112 connected to the processor device 108, and the observation image (endoscopic image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Hence, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

Addition, as illustrated in FIG. 1, the cable part 104 of the endoscope 100 is provided with a forward and backward movement operating part 130 for hooking the index finger of a right hand gripping an operating part 204 of the treatment tool 200, and performing a forward and backward movement operation of the endoscope 100 in a forward-backward direction of the endoscope 100.

The forward and backward movement operating part 130 is disposed at a position adjacent to the operating part 204 of the treatment tool 200, and has, for example, three hooking parts 132 of the same configuration. Each hooking part 132 is formed in an annular shape (ring shape) using elastic materials (for example, rubber materials), and has an opening of such a size that an index finger can pass therethrough.

Accordingly, an operator can pass the index finger of his/her right hand gripping the operating part 204 of the treatment tool 200, through any hooking part 132 of the forward and backward movement operating part 130 to perform the forward and backward movement operation of the endoscope 100, and can easily perform the operation of the treatment tool 200 and the forward and backward movement operation of the endoscope 100 only with his/her right hand. In addition, the endoscope 100 may not include the forward and backward movement operating part 130, and the detailed description of the forward and backward movement operating part 130 will be omitted.

As illustrated in FIG. 1, the treatment tool 200 consists of, for example, forceps, and includes an elongated insertion part 202 (hereinafter referred to as a "treatment tool insertion part 202") that is inserted into a body cavity, an operating part 204 that is provided on the base end side of the treatment tool insertion part 202 and is gripped by an operator, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the outer tube 300 allows the endoscope insertion part 102 and the treatment tool insertion part 202, which are inserted thereinto from the base end side, to be inserted therethrough and delivered from the distal end side. By inserting the outer tube 300 into a body wall and having a base end side thereof disposed outside of the body and a distal end side thereof disposed within the body cavity, the endoscope insertion part 102 and the treatment tool insertion part 202 are guided into the body cavity with one outer tube 300. Additionally, the outer tube 300 includes an interlocking function of moving the endoscope insertion part 102 and the treatment tool insertion part 202 forward and backward in an interlocking manner as will be described below in detail. Accordingly, for example, the endoscope insertion part 102 can also be moved forward and backward by the forward and backward movement operation of only the treatment tool insertion part 202, and a suitable endoscopic image can be obtained without performing the forward and backward movement operation of the endoscope insertion part 102. The details of the configuration and working of the outer tube 300 will be described below.

Figure 3:
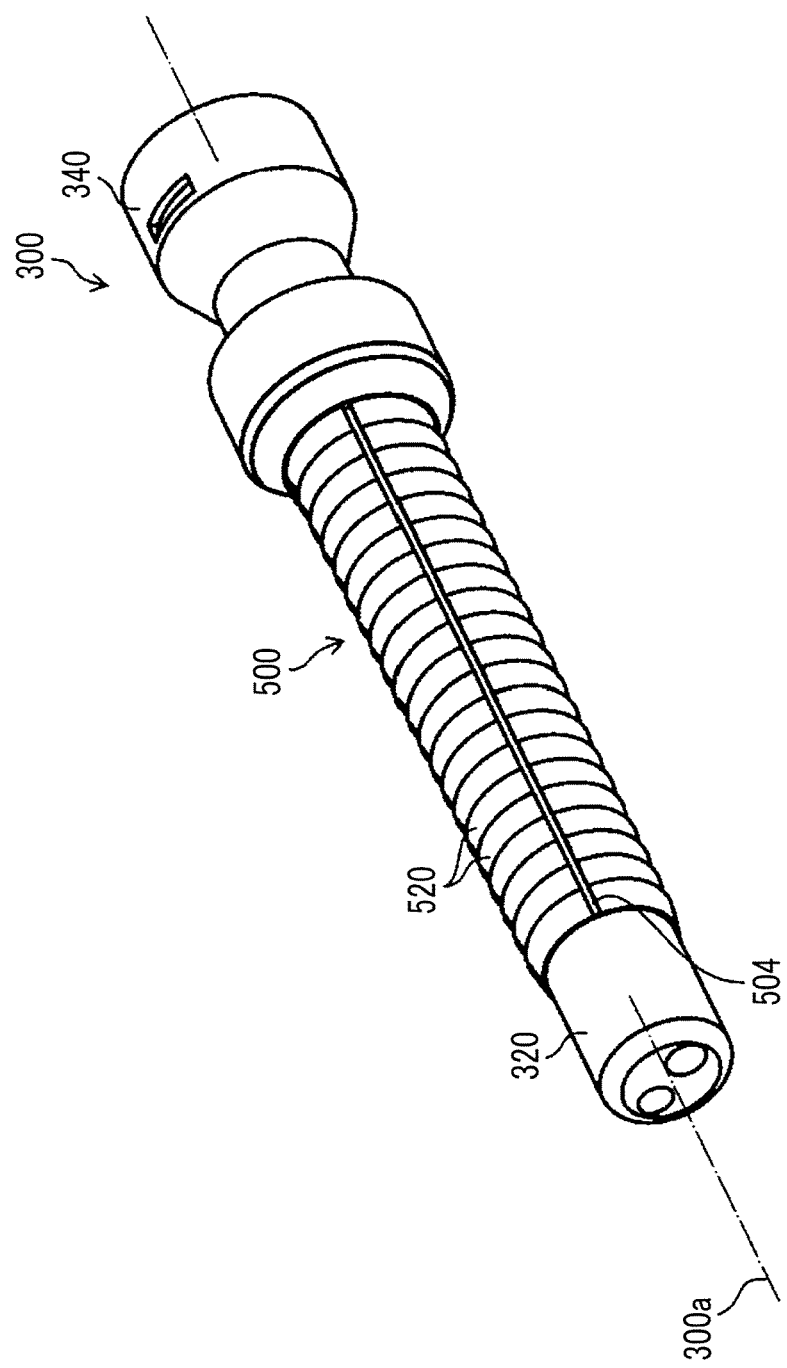
FIG. 3 is a perspective view illustrating a state where an exterior tube is fitted to an outer tube.

The exterior tube 500 illustrated in FIG. 1 is formed in a tubular shape, and as illustrated in FIG. 3, is externally fitted (sheathed) to and fixed to an outer peripheral surface of the outer tube 300 (a long tubular outer tube body 320 to be described below). Although detailed description is omitted, an outer peripheral part of the exterior tube 500 is provided with a number of lateral grooves 520 running along in a circumferential direction, and longitudinal grooves 504 running along an axial direction are provided, for example, in four places in the circumferential direction.

Accordingly, in a state where the outer tube 300 is inserted into a body wall together with the exterior tube 500, a number of the lateral grooves 520 of the exterior tube 500 restrict the forward and backward movement of the exterior tube 500 with respect to the body wall, and the longitudinal grooves in four places of the exterior tube 500 restrict the rotation of the exterior tube 500 in the circumferential direction (around a reference axis 300a) with respect to the body wall. Hence, unintended rotation or forward and backward movement of the outer tube 300 fixed to the exterior tube 500 with respect to the body wall is prevented.

Namely, if the outer tube 300 rotates around the reference axis 300a (around the axis) unintentionally with respect to the body wall or moves forward and backward in the direction (axial direction) of the reference axis 300a when the operation of the treatment tool 200, or the like is performed by inserting the endoscope insertion part 102 and the treatment tool insertion part 202 through the outer tube 300 after the outer tube 300 (long tubular outer tube body 320) is inserted into the body wall, there is a problem that the position of a distal end of the endoscope insertion part 102 may fluctuate and an observation visual field may fluctuate unintentionally. The exterior tube 500 prevents such unintended fluctuation of the observation visual field.

Figure 4:
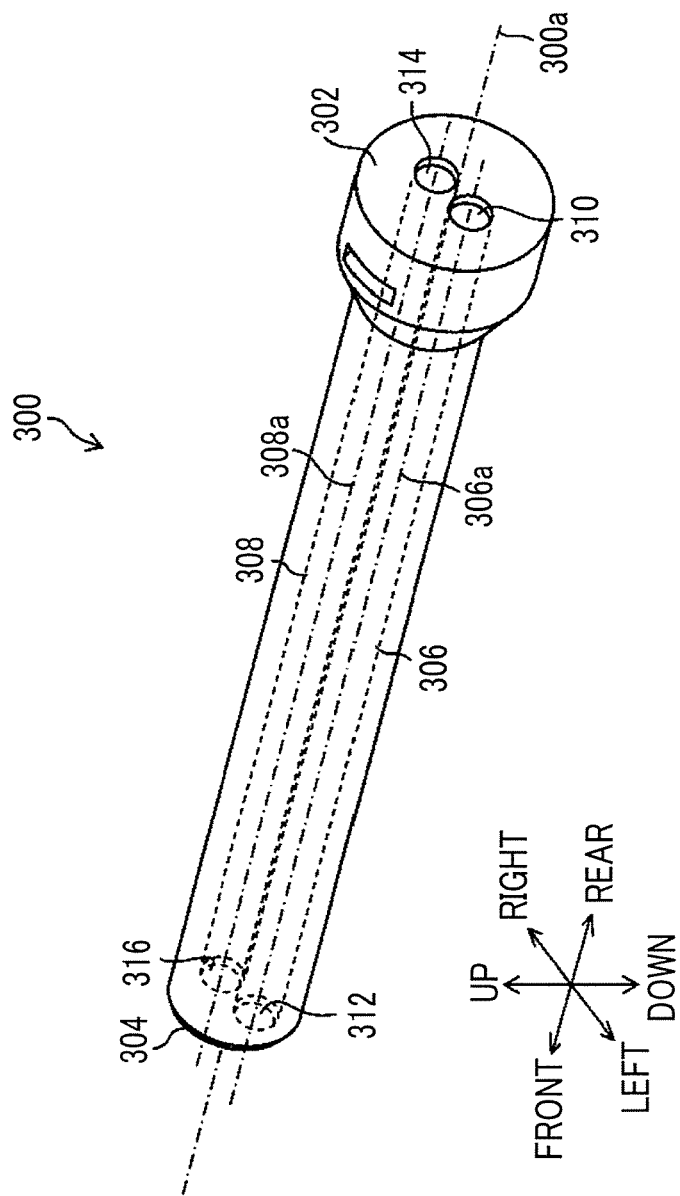
FIG. 4 is an external perspective view illustrating the outer tube.

FIG. 4 is an external perspective view illustrating the outer tube 300.

As illustrated in this drawing, the outer tube 300 has an elongated cylindrical shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a indicating a longitudinal axis that is a central axis of the outer tube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axis of the endoscope insertion part 102 and the central axis of the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are disposed on the same plane. However, a configuration in which the reference axis 300a, the endoscope insertion axis 306a, and the treatment tool insertion axis 308a are disposed on the same plane may not be adopted.

In addition, regarding the position and orientation of a space where the outer tube 300 has been disposed, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the outer tube 300 is provided with a first base end opening 310 that is a base end opening that allows the endoscope insertion part 102 to be inserted into the endoscope insertion passage 306 therethrough, and a second base end opening 314 that is base end opening that allows the treatment tool insertion part 202 to be inserted into the treatment tool insertion passage 308 therethrough.

The distal end surface 304 of the outer tube 300 is provided with a first distal end opening 312 that is a distal end opening that allows the endoscope insertion part 102 inserted into the endoscope insertion passage 306 to be delivered to the outside therethrough, and a second distal end opening 316 that is a distal end opening that allows the treatment tool insertion part 202 inserted into the treatment tool insertion passage 308 to be delivered to the outside therethrough.

Figure 5:
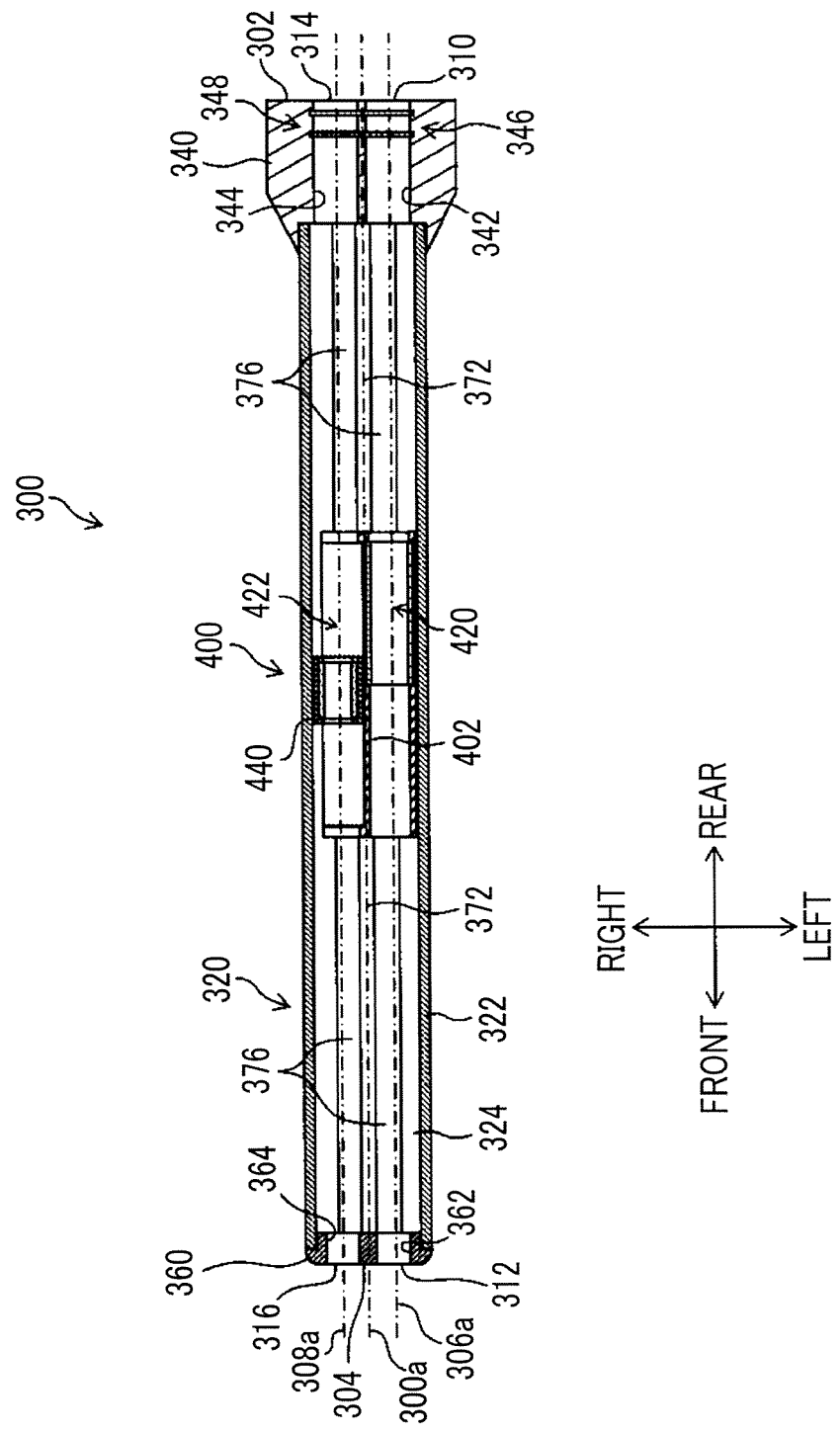
FIG. 5 is a cross sectional view illustrating the internal structure of the outer tube.

FIG. 5 is a cross sectional view illustrating the internal structure of the outer tube 300, and illustrates a cross section cut in a plane that includes the reference axis 300a and is orthogonal to an upward-downward direction (cut in a leftward-rightward direction along the reference axis 300a).

As illustrated in this drawing, the outer tube 300 has a long tubular outer tube body 320 that occupies substantially the entire area in the forward-backward direction, a base end cap 340 that is attached to a rear end (base end) of the outer tube 300, a distal end cap 360 that is attached to a distal end part, and a slider 400 that is one form of the interlocking member disposed inside the outer tube 300.

The long tubular outer tube body 320 is formed in an elongated cylindrical shape having the reference axis 300a as a central axis using hard resins, metals, or the like, and has an outer wall 322 that surrounds an outer periphery, and a cavity part 324 that penetrates from a base end of the long tubular outer tube body 320 to a distal end thereof.

The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the long tubular outer tube body 320 using hard resins, metals, or the like, and a rear end surface thereof constitutes the base end surface 302 of the outer tube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described first base end opening 310, and an opening of the through-hole 344 is equivalent to the above-described second base end opening 314.

Additionally, the through-holes 342 and 344 are provided with valve members 346 and 348. The valve members 346 and 348, for example, open only in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a distal end surface thereof constitutes the distal end surface 304 of the outer tube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described first distal end opening 312, and an opening of the through-hole 364 is equivalent to the second distal end opening 316.

In addition, the long tubular outer tube body 320, the base end cap 340, and the distal end cap 360 show one form of constituent members that constitutes the outer tube body of the outer tube 300, and the outer tube body is not limited to the above configuration. For example, the long tubular outer tube body 320 and the base end cap 340 or the long tubular outer tube body 320 and the distal end cap 360 may be integrally formed, or may be integrally formed in their entirety.

Additionally, the outer tube body may have the following configurations.

Namely, the outer tube body has a distal end, a base end, and a longitudinal axis, and includes a first distal end opening and a second distal end opening equivalent to the above-described first distal end opening 312 and second distal end opening 316 that are provided at the distal end of the outer tube body, and a first base end opening and a second base end opening equivalent to the above-described first base end opening 310 and the second base end opening 314 that are provided at the base end of the outer tube body. The outer tube body just has to include an endoscope insertion passage and a treatment tool insertion passage equivalent to the above-described endoscope insertion passage 306 and treatment tool insertion passage 308 that are provided along the longitudinal axis of the outer tube body, that is, the endoscope insertion passage that communicates with the first distal end opening and the first base end opening and allows the endoscope 100 to be inserted therethrough so as to be movable forward and backward, and the treatment tool insertion passage that communicates with the second distal end opening and the second base end opening and allows the treatment tool 200 to be inserted therethrough so as to be movable forward and backward.

The slider 400 is housed within (the cavity part 324) the long tubular outer tube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a non-sensing region where the forward and backward movement of either the endoscope insertion part or the treatment tool insertion part in the forward-backward direction (axial direction) does not interlock with the movement of the other and a sensing region where the forward and backward movement of either the endoscope insertion part or the treatment tool insertion part interlocks with the movement of the other. The slider 400 does not change the relative position of the distal end of the endoscope 100 with respect to the distal end of the treatment tool 200 in the direction of the reference axis 300a of the outer tube 300 in the non-sensing region. That is, the endoscope insertion part 102 is adapted to interlock with the forward and backward movement of the treatment tool insertion part 202 in the axial direction with play by the slider 400.

Figure 6:
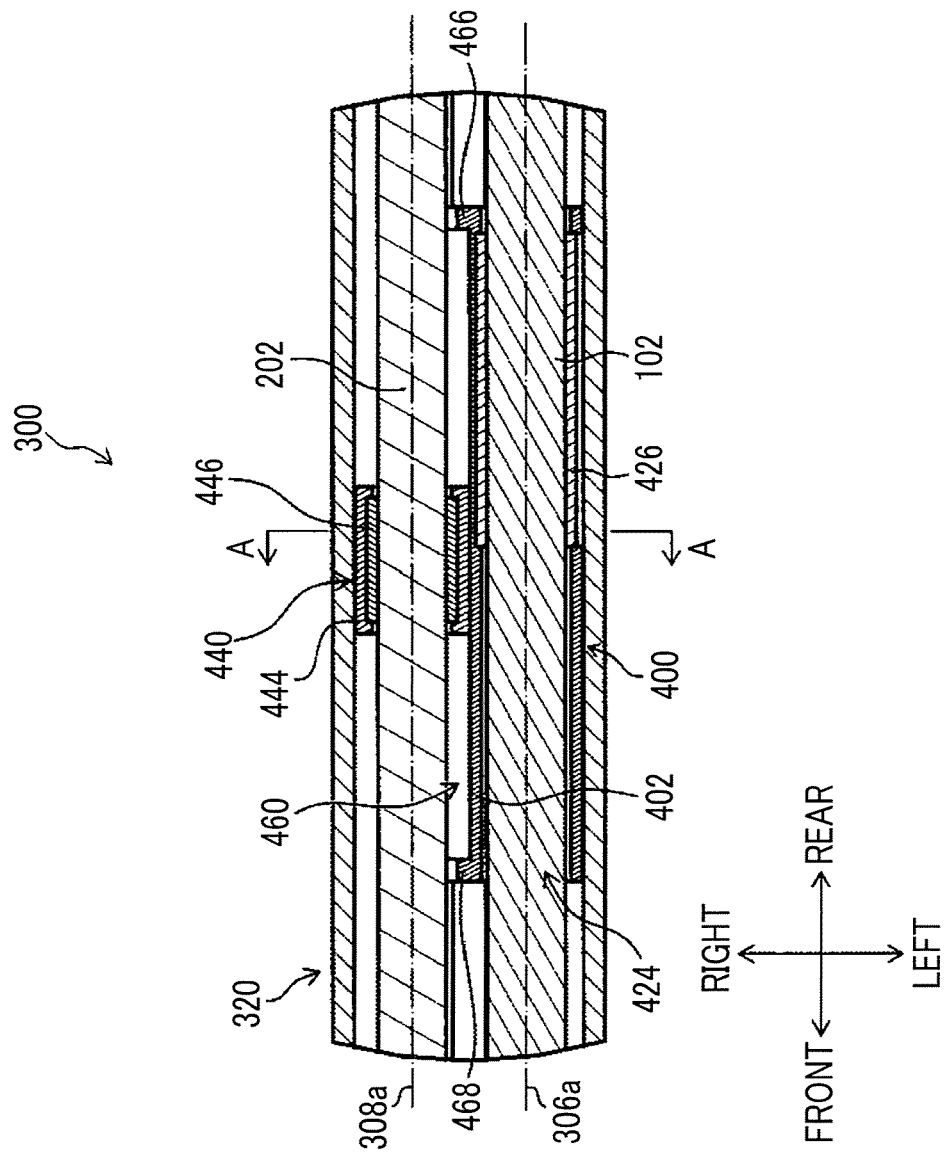
FIG. 6 is an enlarged cross sectional view illustrating a portion of FIG. 5 in an enlarged manner.
Figure 7:
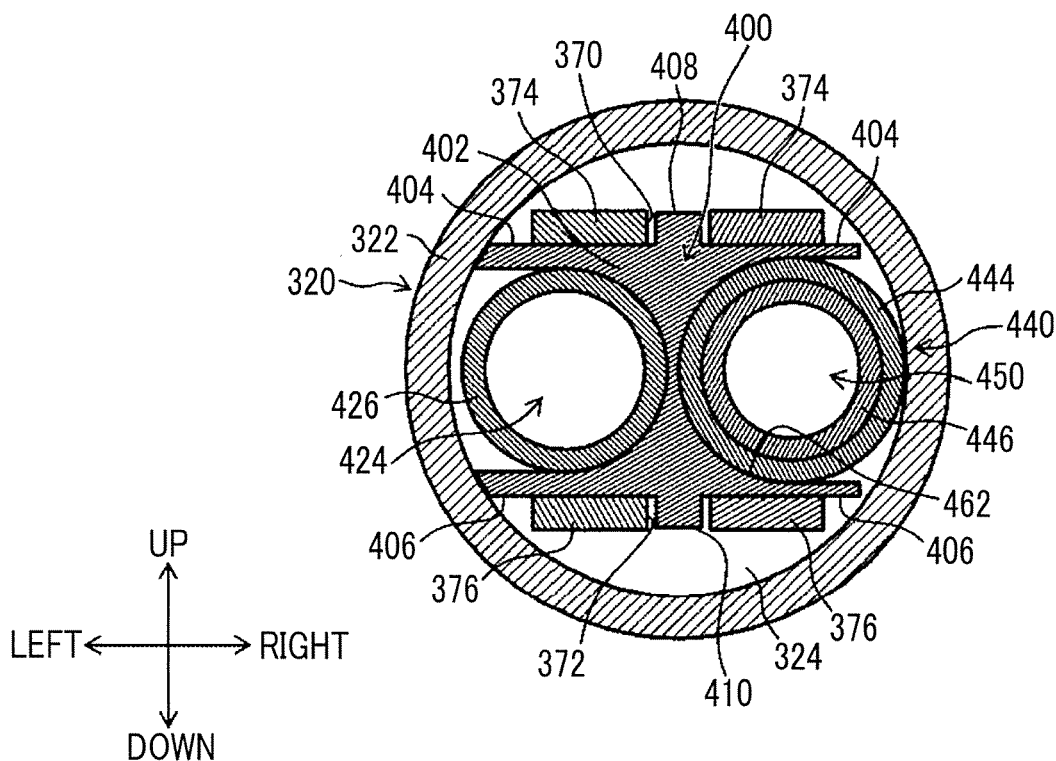
FIG. 7 is a cross sectional view as viewed from arrow A-A in FIG. 6.

FIG. 6 is an enlarged cross sectional view illustrating a portion, in which the slider 400 is disposed in FIG. 5, in an enlarged manner, and illustrates a state where the endoscope insertion part 102 and the treatment tool insertion part 202 have been inserted through the endoscope insertion passage 306 and the treatment tool insertion passage 308, respectively. FIG. 7 is a cross sectional view as seen from arrow A-A in FIG. 6.

Figure 8:
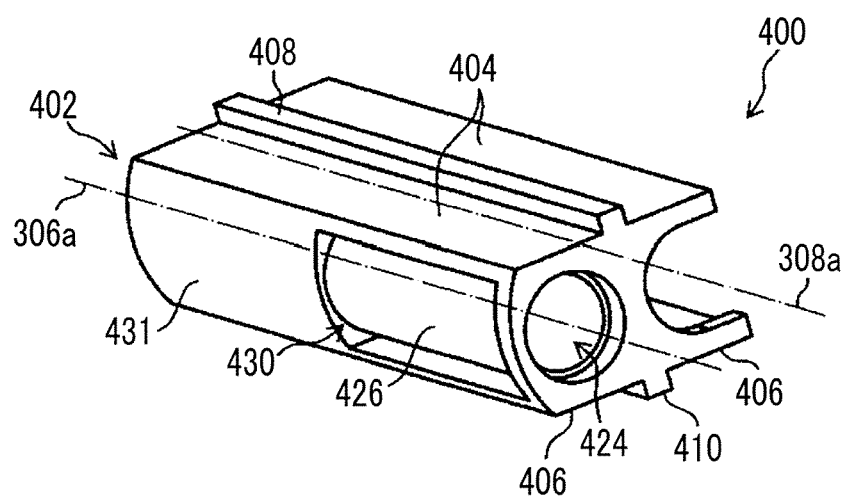
FIG. 8 is a perspective view illustrating a slider (interlocking member) from the rear upper left side.
Figure 9:
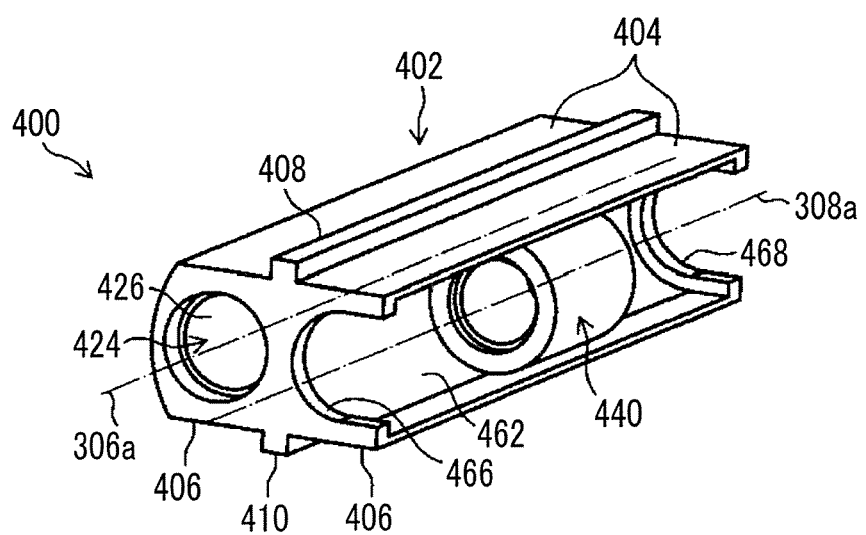
FIG. 9 is a perspective view illustrating the slider (interlocking member) from the rear upper right side.

Additionally, FIGS. 8 and 9 are respectively perspective views illustrating the slider 400 from the rear upper left and from the rear upper right.

As illustrated in these drawings, the slider 400 has a slider body 402 that holds components of the slider 400. As illustrated in FIG. 7, protruding strips 408 and 410 that extend in the direction (forward-backward direction) of the reference axis 300a are formed on a flat upper surface 404 (refer to FIGS. 8 and 9) and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360 and illustrated in FIG. 7, are respectively supported by an upper part and a lower part within the long tubular outer tube body 320, and guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the long tubular outer tube body 320, and the upper surface 404 and the lower surface 406 are disposed in a state where these surfaces have contacted or approached the guide plates 374 and 374 and the guide plates 376 and 376.

Accordingly, the slider 400 is supported so as to be movable forward and backward in the forward-backward direction within the long tubular outer tube body 320, and is supported in a state where the movement of the slider in the upward-downward direction and in the leftward-rightward direction and the rotation of the slider in all directions (directions around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 disposed within the long tubular outer tube body 320, and may be formed in the outer wall 322 of the long tubular outer tube body 320 or may be formed by other configurations.

Additionally, the slider 400, as illustrated in FIG. 5, has a left endoscope-coupling part 420 that is coupled to (engaged with) the endoscope insertion part 102, and a right treatment tool-coupling part 422 that is coupled to (engaged with) the treatment tool insertion part 202.

The endoscope-coupling part 420 provided on the left side of the slider body 402 secures a space serving as the endoscope insertion passage 306, within the long tubular outer tube body 320. Additionally, the endoscope-coupling part 420, as illustrated in FIG. 6, includes a through-hole 424 (refer to FIGS. 7, 8, and 9) into which the endoscope insertion part 102 is inserted, and a pressure-contact member 426 that is fixed to the through-hole 424 and is brought into pressure contact with the outer peripheral surface (side surface) of the endoscope insertion part 102 inserted through the endoscope insertion passage 306.

The pressure-contact member 426 is formed in a cylindrical shape using elastic materials, such as elastic rubber, as illustrated in FIGS. 7 and 8, and is fitted into up to a position coaxial with the through-hole 424 of the slider body 402 from an opening 430 formed on a left side surface 431 of the slider body 402 and fixed to the slider body 402, as illustrated in FIG. 8.

Accordingly, when the endoscope insertion part 102 has been inserted through the endoscope insertion passage 306, as illustrated in FIG. 6, the endoscope insertion part 102 is inserted through the through-hole 424, and the pressure-contact member 426 is brought into pressure contact with (engaged with) the outer peripheral surface of the endoscope insertion part 102. Accordingly, the central axis of the endoscope insertion part 102 is disposed coaxially with the endoscope insertion axis 306a.

The endoscope insertion part 102 and the slider 400 (slider body 402) are coupled to (engaged with) each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupling part 422 provided on the right side of the slider body 402 as illustrated in FIG. 5, as illustrated in FIG. 6, includes a sleeve 440 (refer to FIGS. 7 and 9) that is coupled to the treatment tool insertion part 202, and a guide part 460 that guides the sleeve 440 so as to be movable forward and backward in the forward-backward direction.

The sleeve 440, as illustrated in FIG. 7, includes a sleeve body 444 (frame body) formed in a cylindrical shape, and a pressure-contact member 446 fixed to the inside of the sleeve body 444. The pressure-contact member 446 is formed in a cylindrical shape using elastic materials, such as elastic rubber.

Accordingly, when the treatment tool insertion part 202 has been inserted through the treatment tool insertion passage 308, as illustrated in FIG. 6, the treatment tool insertion part 202 is inserted through the inside (the through-hole 450 of FIG. 7) of the pressure-contact member 446, the pressure-contact member 446 is brought into pressure contact with (engaged with) the outer peripheral surface of the treatment tool insertion part 202. Accordingly, the central axis of the treatment tool insertion part 202 is disposed coaxially with the treatment tool insertion axis 308a.

The treatment tool insertion part 202 and the sleeve 440 are coupled to each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupling part 422, as illustrated in FIGS. 7 and 9, is formed by a space surrounded by a guide surface 462 of the slider body 402 that extends in the direction of the reference axis 300a (treatment tool insertion axis 308a), within the cavity part 324 of the long tubular outer tube body 320, and an inner peripheral surface of the long tubular outer tube body 320. The sleeve 440 is housed and disposed in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIGS. 6 and 9, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 disposed in the space of the guide part 460 moves forward and backward in the forward-backward direction.

Hence, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

The working of the slider 400 configured as described above will be described together with the operation when the treatment of a diseased site within a patient's body cavity is performed using the surgical apparatus for an endoscope 10.

Figure 13:
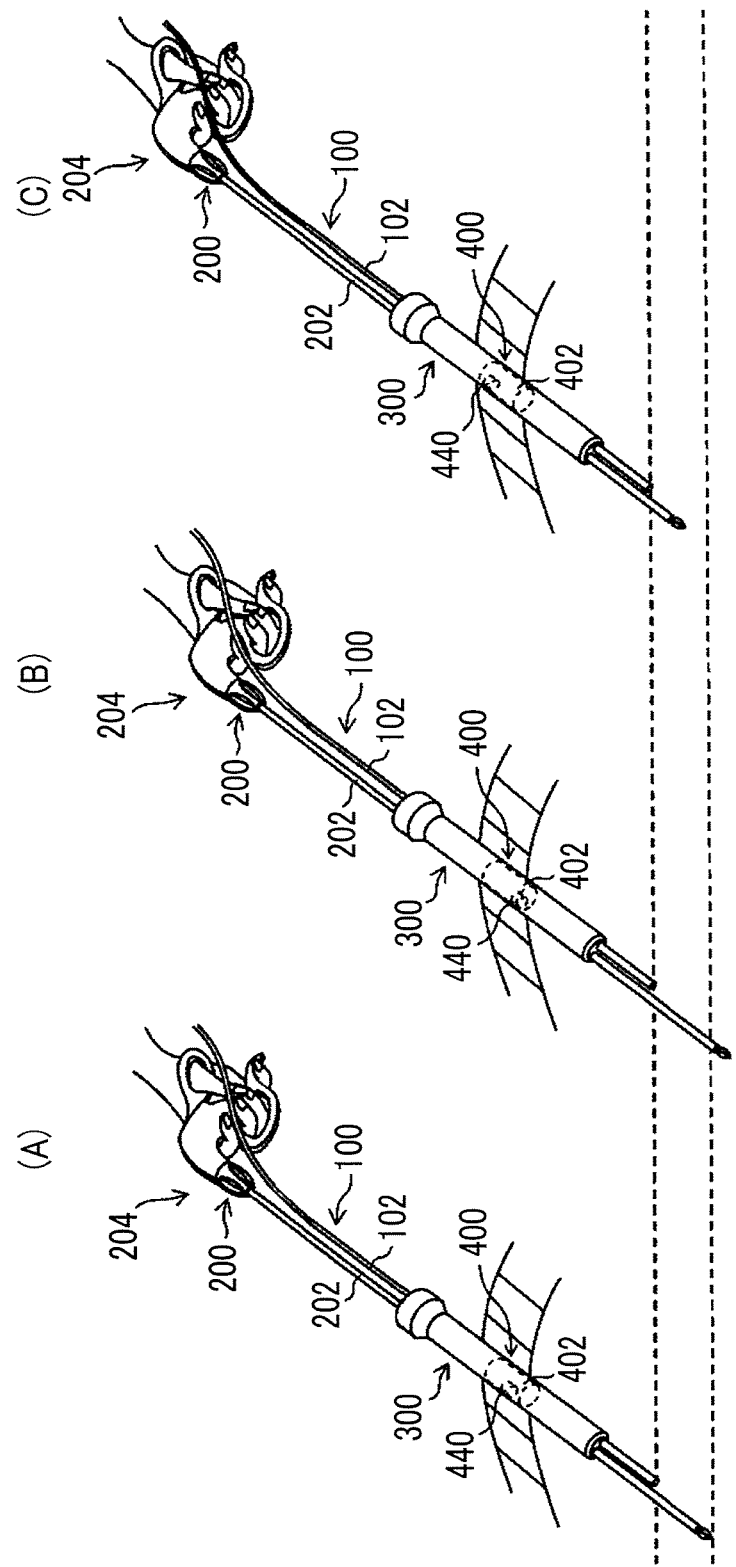
FIG. 13 is an explanatory view illustrating a state of the operation when the treatment of a diseased site within a patient's body cavity is performed using the surgical apparatus for an endoscope.
Figure 14:
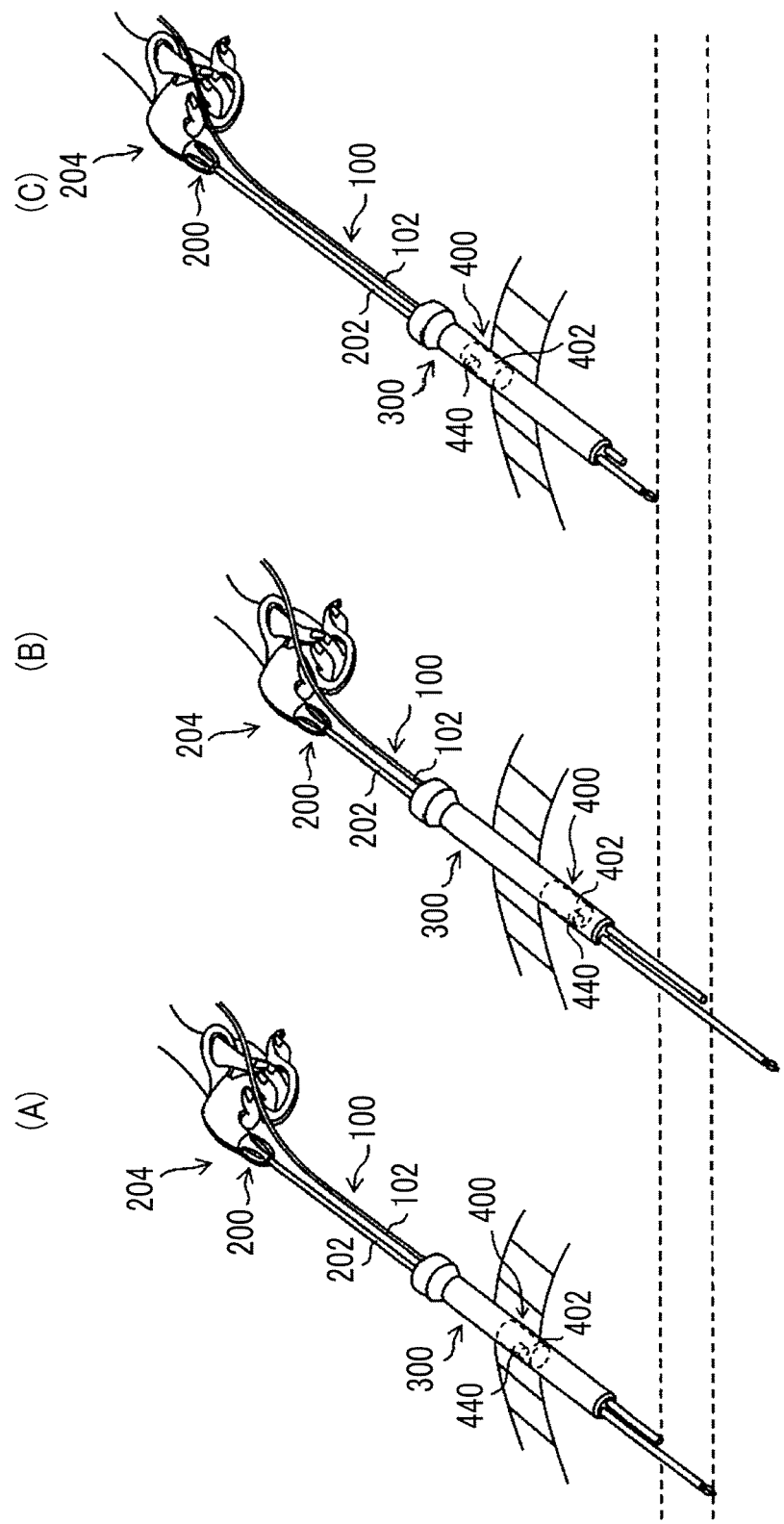
FIG. 14 is an explanatory view illustrating a state of the operation when the treatment of the diseased site within the patient's body cavity is performed using the surgical apparatus for an endoscope.

First, as illustrated in (A) part of FIG. 13, after the outer tube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the outer tube 300, and the endoscope insertion part 102 and the treatment tool insertion part 202 are mounted on the outer tube 300. In this case, the endoscope insertion part 102 is coupled to the slider body 402 of the slider 400, and the treatment tool insertion part 202 is coupled to the sleeve 440 of the slider 400. In addition, although the exterior tube 500 is not illustrated in FIG. 13, and FIG. 14 illustrated therebelow, the exterior tube 500 is fitted to the outer tube 300 as illustrated in FIG. 3. However, it is also possible to use the outer tube 300 without fitting the exterior tube 500 thereto. Additionally, the forward and backward movement operating part 130 of the endoscope 100 is also omitted in the drawings.

Figure 10:
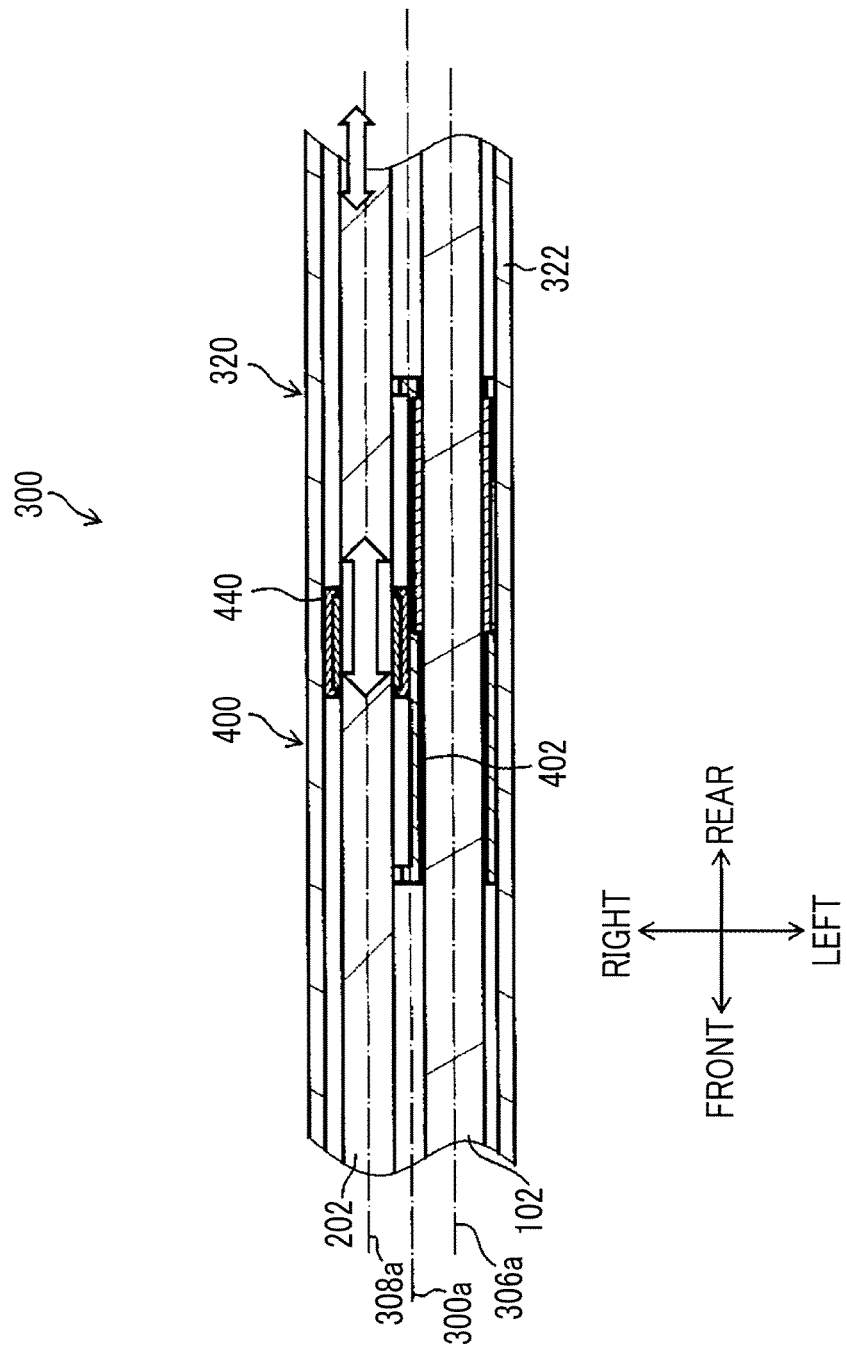
FIG. 10 is an explanatory view used for the description of the working of the slider (interlocking member).

Supposing the state of (A) part of FIG. 13 is a state where the sleeve 440 reaches neither the front end nor the rear end of the movable range thereof with respect to the slider body 402 (guide part 460) as illustrated in FIG. 10, and if an operator minutely moves the treatment tool insertion part 202 forward with his/her hand that is gripping the operating part 204 of the treatment tool 200, the slider body 402 does not move with respect to the outer tube 300 (long tubular outer tube body 320), but only the sleeve 440 moves forward with respect to the slider body 402 within the movable range thereof with respect to the slider body 402. For that reason, with respect to the forward movement of the treatment tool insertion part 202 until the sleeve 440 reaches the front end of the movable range thereof with respect to the slider body 402, as illustrated in (B) part of FIG. 13, only the treatment tool insertion part 202 moves forward in a state where the endoscope insertion part 102 is stationary. That is, the slider 400 has the non-sensing region where the endoscope insertion part 102 does not interlock with the forward and backward movement of the treatment tool insertion part 202, and the forward movement operation of the treatment tool 200 at this time becomes a forward and backward movement operation of the slider 400 in the non-sensing region.

Similarly, supposing the state of (A) part of FIG. 13 is a state where the sleeve 440 reaches neither the front end nor the rear end of the movable range thereof with respect to of the slider body 402 (guide part 460) as illustrated in FIG. 10, and if the operator minutely moves the treatment tool insertion part 202 backward with his/her hand that is gripping the operating part 204 of the treatment tool 200, the slider body 402 does not move with respect to the outer tube 300 (long tubular outer tube body 320), but only the sleeve 440 moves backward with respect to the slider body 402 within the movable range thereof with respect to the slider body 402. For that reason, with respect to the backward movement of the treatment tool insertion part 202 until the sleeve 440 reaches the rear end of the movable range thereof with respect to the slider body 402, as illustrated in (C) part of FIG. 13, only the treatment tool insertion part 202 moves backward in a state where the endoscope insertion part 102 is stationary. That is, the backward movement operation of the treatment tool 200 at this time becomes a backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of a site to be observed, such as a distal end site of the treatment tool 200 or a lesioned site, to be displayed on the monitor 112 as an endoscopic image does not vary, and the size of an image of the site to be observed can be prevented from fluctuating according to minute displacement of the treatment tool 200. Accordingly, a sense of perspective can be suitably maintained, and a stable endoscopic image can be provided.

Figure 11:
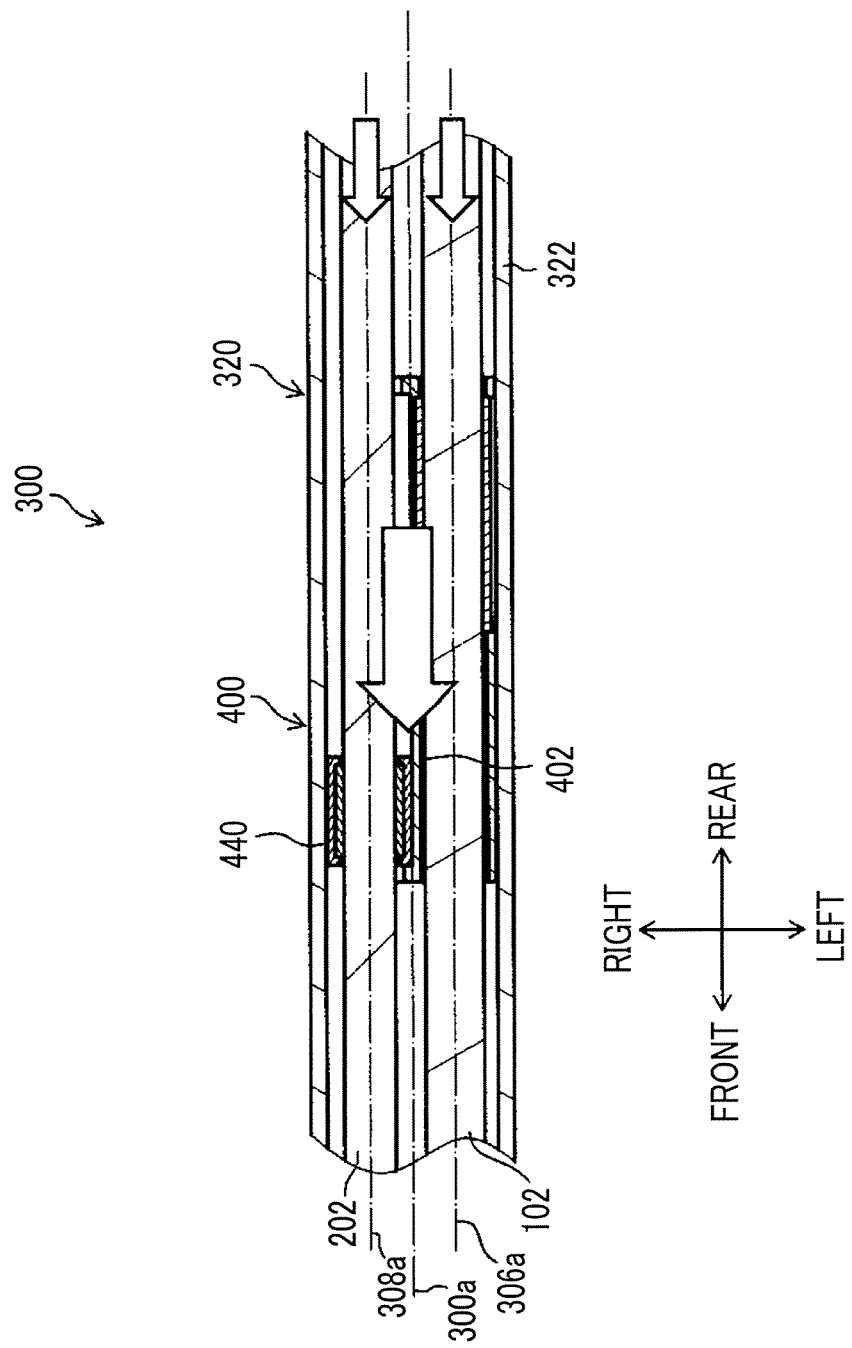
FIG. 11 is an explanatory view used for the description of the working of the slider (interlocking member).

Meanwhile, if the operator greatly moves the treatment tool insertion part 202 forward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the front end of the movable range thereof with respect to the slider body 402 as illustrated in FIG. 11 is brought into after the forward movement of the sleeve 440 of the slider 400 in the non-sensing region until it abuts against the front end of the movable range. Then, if the treatment tool insertion part 202 further moves forward, the sleeve 440 and the slider body 402 moves forward with respect to the long tubular outer tube body 320 together with the treatment tool insertion part 202. As a result, the endoscope insertion part 102 moves forward in an interlocking manner with the treatment tool insertion part 202. For that reason, with respect to the forward movement of the treatment tool insertion part 202 after the sleeve 440 reaches the front end of the movable range thereof with respect to the slider body 402, the endoscope insertion part 102 moves forward in an interlocking manner with the treatment tool insertion part 202 as illustrated in (B) part of FIG. 14, compared to the state of (A) part of FIG. 14 illustrating the same state as (A) part of FIG. 13. That is, the slider 400 has the sensing region where the endoscope insertion part 102 interlocks with the forward and backward movement of the treatment tool insertion part 202, and the forward movement operation of the treatment tool 200 at this time becomes a forward movement operation of the slider 400 in the sensing region.

Figure 12:
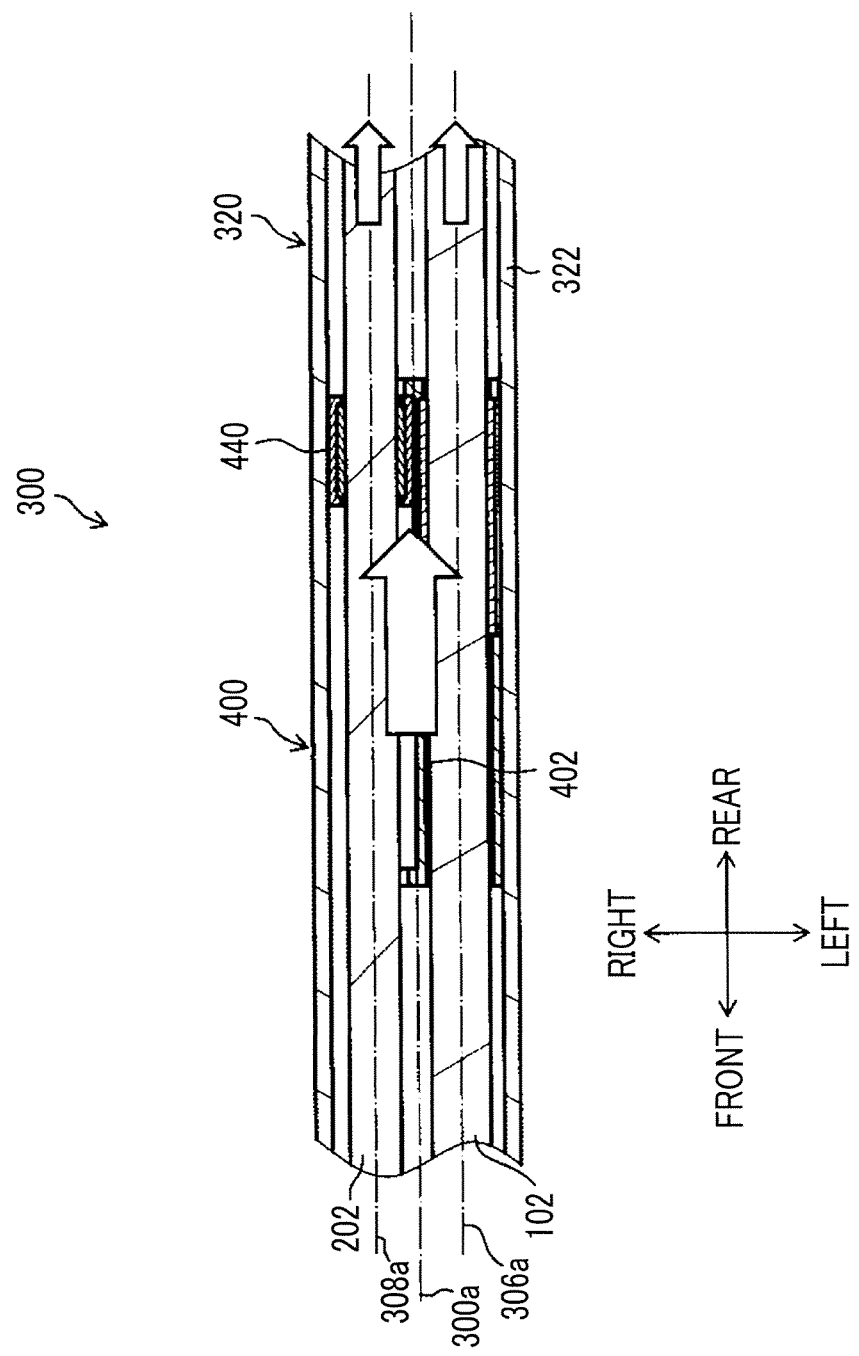
FIG. 12 is an explanatory view used for the description of the working of the slider (interlocking member).

Similarly, if the operator greatly moves the treatment tool insertion part 202 backward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the rear end of the movable range thereof with respect to the slider body 402 as illustrated in FIG. 12 is brought into after the backward movement of the sleeve 440 of the slider 400 in the non-sensing region until it abuts against the rear end of the movable range. Then, if the treatment tool insertion part 202 further moves backward, the sleeve 440 and the slider body 402 moves backward with respect to the long tubular outer tube body 320 together with the treatment tool insertion part 202. As a result, the endoscope insertion part 102 moves backward in an interlocking manner with the treatment tool insertion part 202. For that reason, with respect to the backward movement of the treatment tool insertion part 202 after the sleeve 440 reaches the rear end of the movable range thereof with respect to the slider body 402, as illustrated in (C) part of FIG. 14, the endoscope insertion part 102 moves backward in an interlocking manner with the treatment tool insertion part 202. That is, the backward movement operation of the treatment tool 200 at this time becomes a backward movement operation of the slider 400 in the sensing region.

Therefore, since the endoscope 100 moves forward and backward with respect to a large forward and backward movement operation of the treatment tool 200, that is, the forward and backward movement operation thereof in the sensing region, the range of a site to be observed that appears in an endoscopic image to be displayed on the monitor 112 is continuously changed so as to follow the forward and backward movement of the treatment tool 200. Since the size of images of sites to be observed other than the distal end site of the treatment tool 200 that appears in the endoscopic image according to the operation of the treatment tool 200, or the size of the range of the site to be observed varies, the operator can simply obtain a desired image.

As described above, in a case where the displacement of the treatment tool insertion part 202 in the axial direction is large (in a case where a large amplitude of forward and backward movement has been performed) when an operator has moved the treatment tool insertion part 202 forward and backward in the axial direction, the endoscope insertion part 102 also moves in an interlocking manner forward, backward, up, down, right, and left. Thus, the visual field, orientation, and the like of the endoscope 100 can be changed as intended by an operator. Additionally, the visual field is always given to pick up an image of the distal end site of the treatment tool 200 and consequently, an image that is optimal for treatment is automatically provided. In a case where it is desired to check sites other than a site to be treated, the checking can be performed by moving the treatment tool insertion part 202, and an operator can perform operations as desired. Hence, an assistant (endoscopic technician) who operates the endoscope 100 apart from the operator can be made unnecessary, and a troublesome condition in which the operator should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, an endoscopic image can be prevented from fluctuating unnecessarily, a sense of perspective can be suitably maintained, and a stable endoscopic image can be provided.

Subsequently, the forward and backward movement operation of the endoscope 100 in the non-sensing region of the slider 400 using the forward and backward movement operating part 130 of the endoscope 100 will be described.

Figure 15:
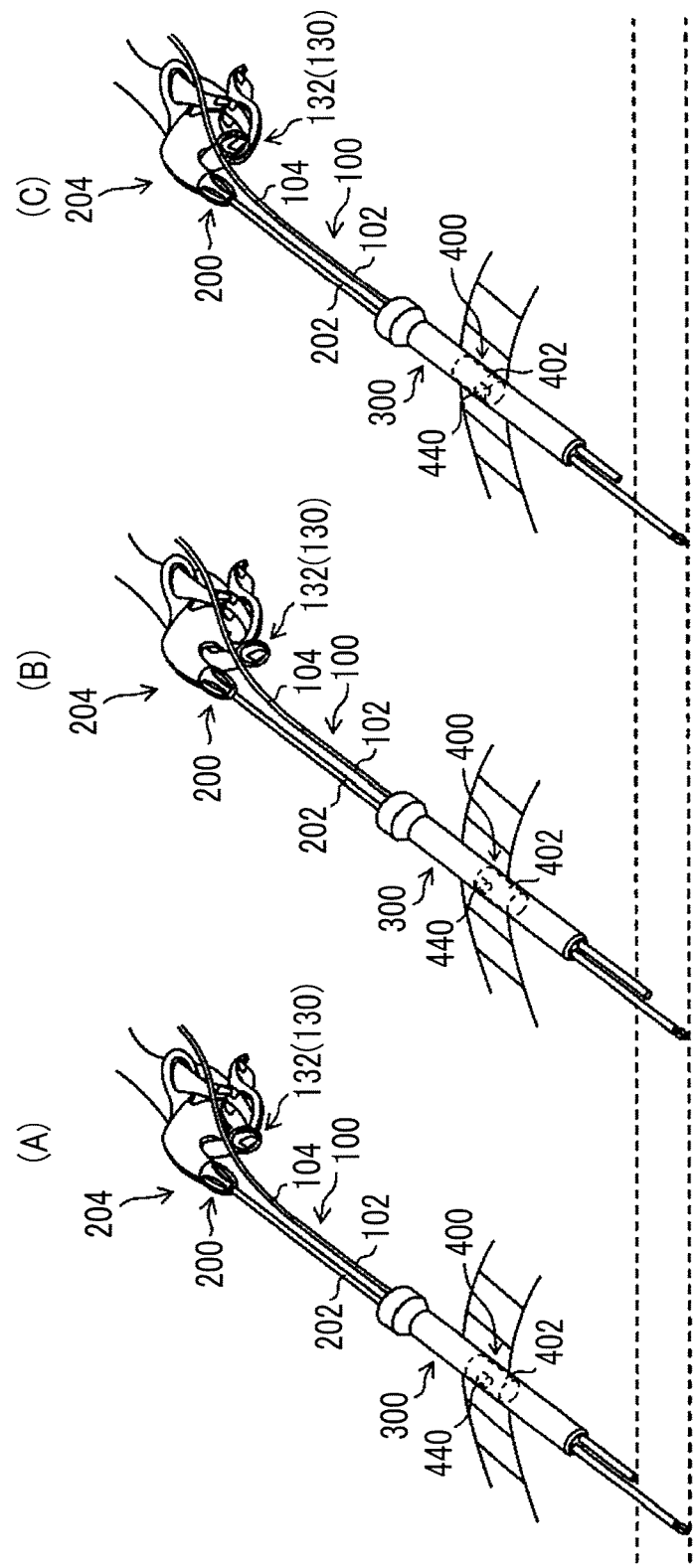
FIG. 15 is an explanatory view illustrating a state of the operation when the treatment of the diseased site within the patient's body cavity is performed using the surgical apparatus for an endoscope.

(A) part of FIG. 15 illustrates that the outer tube 300, the endoscope 100, and the treatment tool 200 are in the same state as those of (A) part of FIG. 13 and (A) part of FIG. 14.

In this state, if the operator passes the index finger of his/her right hand gripping the operating part 204 of the treatment tool 200 into an opening of any hooking part 132 (only one is illustrated in the drawing) of the forward and backward movement operating part 130 of the endoscope 100 and moves his/her index finger forward, the endoscope 100 moves forward. Similarly, with respect to the forward movement of the endoscope 100 in the non-sensing region until the sleeve 440 in the slider 400 abuts against the rear end of the movable range thereof, as illustrated in (B) part of FIG. 15, only the endoscope 100 moves forward in a state where the treatment tool 200 is stationary.

Similarly, if the operator passes the index finger of his/her right hand gripping the operating part 204 of the treatment tool 200 into an opening of any hooking part 132 of the forward and backward movement operating part 130 of the endoscope 100 and moves his/her index finger backward, the endoscope 100 moves backward. Similarly, with respect to the backward movement of the endoscope 100 in the non-sensing region until the sleeve 440 in the slider 400 abuts against the front end of the movable range thereof, as illustrated in (C) part of FIG. 15, only the endoscope 100 moves backward in a state where the treatment tool 200 is stationary.

Hence, the position of the distal end (distal end surface 114) of the endoscope 100 can be moved forward and backward without moving the treatment tool 200 forward and backward, by such forward and backward movement operation of the endoscope 100. Therefore, only the visual field (the range of a site to be observed that appears in the endoscopic image) of the endoscope 100 can be changed. That is, an image of a site to be observed that is displayed on the monitor 112 (appears in the endoscopic image) and the range of the site to be observed can be zoomed in or zoomed out.

Next, a zooming system in the above surgical apparatus for an endoscope 10 will be described.

Figure 16:
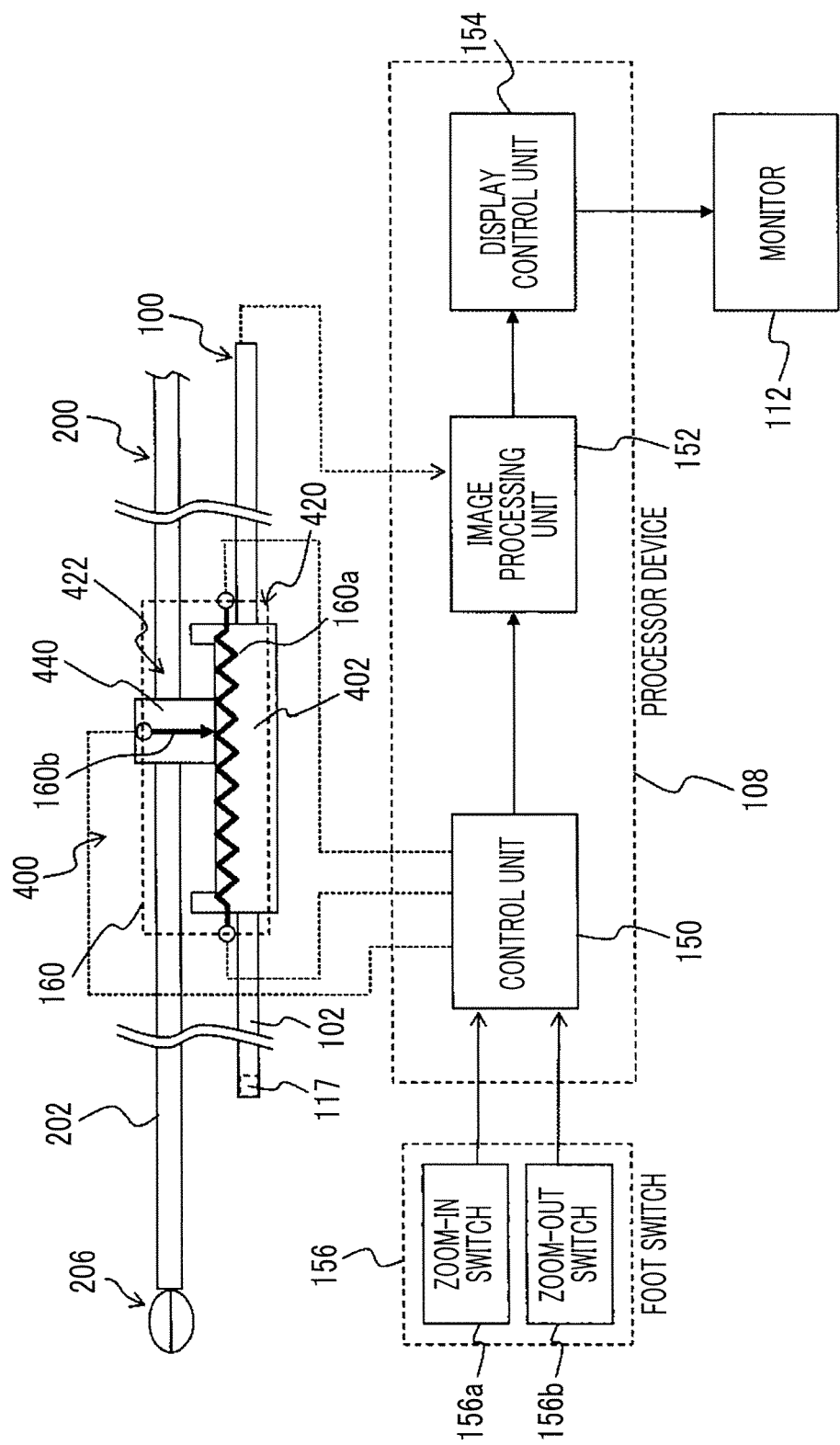
FIG. 16 is an overall configuration view of a zooming system in the surgical apparatus for an endoscope.

FIG. 16 is an overall configuration view of the zooming system in the above surgical apparatus for an endoscope 10. As illustrated in this drawing, the zooming system is constituted with the endoscope 100 that is inserted through at the endoscope insertion passage 306 (refer to FIGS. 4 and 5, and the like) of the outer tube 300 as described above and is coupled to the slider body 402 of the slider 400 via the pressure-contact member 426 (refer to FIG. 6 and the like), detecting means 160 provided in the slider 400, the processor device 108 (refer to FIG. 1) connected to the endoscope 100 via a cable part 104, the monitor 112 connected to the processor device 108, a foot switch 156 connected to the processor device 108, and the like.

The endoscope 100 has a solid image pickup element 117 (hereinafter simply referred to as an "image pickup element 117") at a distal end part thereof as a constituent element of the observation part as described above, and an image of a site to be observed that is observed via the observation window 116 (refer to FIG. 2) is picked up by the image pickup element 117, and the image is given to the processor device 108 as an endoscopic image.

The processor device 108 includes a control unit 150, an image processing unit 152, and a display control unit 154.

The image processing unit 152 has zooming means for carrying out electronic zooming processing, and the zoom magnification factor of the endoscopic image (output image) is changed by performing the electronic zooming processing on an original image given as the endoscopic image from the endoscope 100 according to an instruction given from the control unit 150 as will be described below.

Here, the electronic zooming means the processing of changing the zoom magnification factor of the output image (zooming in or zooming out the endoscopic image) by cutting out an image in a partial range as the output image from the original image given by the endoscope 100, and zooms in the output image to a specified image size and by enlarging or reducing a range where the output image is cut out from the original image.

The image processing unit 152 gives the endoscopic image (output image), which is obtained performing such electronic zooming processing, to the display control unit 154.

The display control unit 154 converts the output image given as the endoscopic image from the image processing unit 152 in the form of display signals, and outputs the converted display signals to the monitor 112. Accordingly, the endoscopic image (output image) subjected to the electronic zooming processing is displayed on the monitor 112.

The detecting means 160 provided in the slider 400 is detecting means for detecting the relative position of the endoscope-coupling part 420 with respect to the treatment tool-coupling part 422 in the slider 400, as information showing the relative position of the distal end of the endoscope 100 with respect to the distal end of the treatment tool 200 in the direction (refer to FIG. 5 and the like) of the reference axis 300a of the outer tube 300. Moreover, the position of the endoscope-coupling part 420 is equivalent to the position of the slider body 402 coupled to the endoscope insertion part 102 via the above-described pressure-contact member 426, and the position of the treatment tool-coupling part 422 is equivalent to the position of the sleeve 440 coupled to the treatment tool insertion part 202 via the above-described pressure-contact member 446. Hence, the detecting means 160 detects the position of the sleeve 440 in the direction of the reference axis 300a with respect to the slider body 402, as information showing the relative position of the endoscope-coupling part 420 with respect to the treatment tool-coupling part 422 in the slider 400. In addition, in the following, in cases where positions are simply mentioned regarding respective members, these positions indicate positions in the direction of the reference axis 300a.

The detecting means 160 has, for example, a resistor 160a installed in the slider body 402, and a slider 160b installed in the sleeve 440, as illustrated in FIG. 16. The resistor 160a is, for example, installed in the direction of the reference axis 300a on a guide surface 462 (refer to FIG. 9) of the slider body 402. The slider 160b is, for example, installed on an outer peripheral surface of the sleeve 440, and the slider 160b slidably comes in contact with the resistor 160a with one point of the resistor as a contact point. If the sleeve 440 moves within the movable range thereof with respect to the slider body 402 as described above, the position of the contact point where the slider 160b come in contact with the resistor 160a moves.

The resistor 160a and the slider 160b of the detecting means 160 are connected to the control unit 150 of the processor device 108, and a certain voltage output from the control unit 150 is applied to the resistor 160a. Accordingly, a certain potential difference is caused between both ends of the resistor 160a, and a detection signal of a voltage value according to the position of the contact point between the resistor 160a and the slider 160b is given from the slider 160b to the control unit 150. The control unit 150 detects the position of the sleeve 440 with respect to the slider body 402 on the basis of the voltage value of the detection signal given from the slider 160b.

In addition, the detecting means 160 is not limited to the configuration of the present embodiment, and just has to be able to detect the information showing the relative position of the distal end of the endoscope 100 with respect to the distal end of the treatment tool 200 in the direction of the reference axis 300a of the outer tube 300. For example, the way of reflecting the treatment tool 200 to be reflected in the endoscopic image in the image processing unit 152 can be detected by image processing, and the relative position of the distal end of the endoscope 100 with respect to the distal end of the treatment tool 200 can also be detected on the basis of the reflecting way.

The foot switch 156 is, for example, a zoom operating means in which an operator operates the zooming means (electronic zooming) in the image processing unit 152 with his/her foot, and has an zoom-in switch 156a that is a first operation switch and a zoom-out switch 156b that is a second operation switch, which are switched on when its operation (depression operation) is performed and switched off when its operation is not performed. The zoom-in switch 156a is a switch that zooms in the endoscopic image, and the zoom-out switch 156b is a switch that zooms out the endoscopic image. Operation signals showing the ON/OFF state of the zoom-in switch 156a and the zoom-out switch 156b are given to the control unit 150 of the processor device 108. In addition, the zoom operating means may be zoom operating means provided in the endoscope 100 without being limited to the foot switch 156, and can be disposed at arbitrary positions and operated by arbitrary methods.

The control unit 150 instructs the image processing unit 152 about the zoom magnification factor on the basis of an operation signal given from the foot switch 156. The image processing unit 152 changes the zoom magnification factor of the endoscopic image given from the endoscope 100 so as to have the zoom magnification factor specified from the control unit 150.

For example, while the zoom-in switch 156a is continuously operated, an operation signal showing that the zoom-in switch 156a is in an ON state is continuously given to the control unit 150. In this case, the control unit 150 continuously increases the zoom magnification factor to be specified for the image processing unit 152. Accordingly, the zoom magnification factor of an output image increases continuously in the image processing unit 152, the size of an image of a site to be observed that appears in the output image is continuously zoomed in, and the size of the range of the site to be observed that appears in the output image is continuously zoomed out.

Similarly, while the zoom-out switch 156b is continuously operated, an operation signal showing that the zoom-out switch 156b is in an ON state is continuously given to the control unit 150. In this case, the control unit 150 continuously reduces the zoom magnification factor to be specified for the image processing unit 152. Accordingly, the zoom magnification factor of an output image decrease continuously in the image processing unit 152, the size of an image of a site to be observed that appears in the output image is continuously zoomed out, and the size of the range of the site to be observed that appears in the output image is continuously zoomed in.

In addition, whenever the zoom-in switch 156a or the zoom-out switch 156b is turned on, the zoom magnification factor may increase or decrease to a discrete value, and if the zoom-in switch 156a or the zoom-out switch 156b is turned on one degree (one push), a predetermined zoom magnification factor may be instantaneously set for each switch.

Moreover, in a case where the relative position (relative position of the endoscope-coupling part 420 with respect to the treatment tool-coupling part 422 in the slider 400) of the distal end of the endoscope 100 with respect to the distal end of the treatment tool 200 deviates from a predetermined region, a zooming state may be released. In this case, the operation of releasing the zooming state to return the zooming state to an original state before a change in the zoom magnification factor can be simplified, and time and efforts for a zooming operation can be reduced.

Additionally, the control unit 150 includes switching means that detects the position of the sleeve 440 with respect to the slider body 402 on the basis of the detection signal from the detecting means 160 as described above, and switches between activation and deactivation of the operation of the zooming means by the foot switch 156, on the basis of the detected position (detection result).

Here, activating the operation of the zooming means indicates changing the zoom magnification factor of the endoscopic image (output image) according to the operation signal from the foot switch 156 as described above. On the other hand, deactivating the operation of the zooming means indicates not receiving the operation signal from the foot switch 156. Additionally, the zoom magnification factor being one time indicates generating an output image of a specified image size without carrying out the electronic zooming processing on the original image given from the endoscope 100, or making an image cut out of a cutoff range of a predetermined reference size into an output image of a specified image size. In addition, in a case where a change to a zoom magnification factor smaller than one time is enabled, a range smaller than a total range of the original image given as the endoscopic image from the endoscope 100 is defined as a cutoff range of a standard size, and a zoom magnification factor when an image in the cutoff range is an output image is defined as one time.

Two different forms are considered as switching conditions of switching between the activation and deactivation of the operation of the zooming means as follows regarding the processing of the control unit 150 serving as this switching means.

Figure 17:
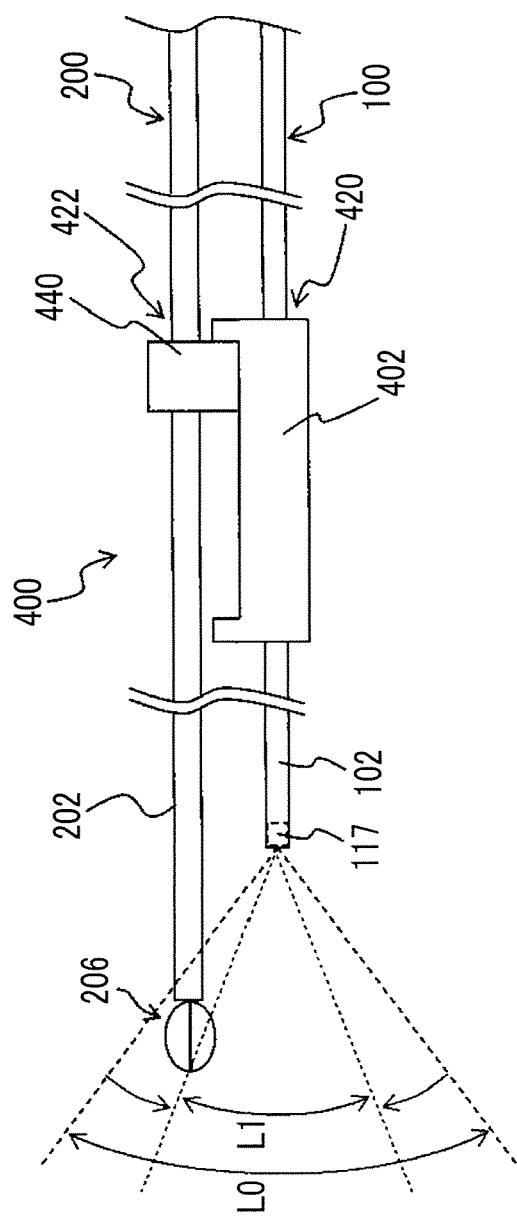
FIG. 17 is a view illustrating a state when the relative position of an endoscope-coupling part with respect to a treatment tool-coupling part is a first position.

First, the relative position of the endoscope-coupling part 420 with respect to the treatment tool-coupling part 422 when the distal end of the endoscope 100 approaches the distal end of the treatment tool 200 most is defined as a first position. That is, the relative position of the endoscope-coupling part 420 with respect to the treatment tool-coupling part 422 being the first position indicates a state where the sleeve 440 of the slider 400 reaches the rear end of the movable range thereof with respect to the slider body 402 as illustrated in FIG. 17.

Additionally, the relative position of the endoscope-coupling part 420 with respect to the treatment tool-coupling part 422 when the distal end of the endoscope 100 is separated from the distal end of the treatment tool 200 most is defined as a second position. That is, the relative position of the endoscope-coupling part 420 with respect to the treatment tool-coupling part 422 being the second position indicates a state where the sleeve 440 of the slider 400 reaches the front end of the movable range thereof with respect to the slider body 402 as illustrated in FIG. 18.

In addition, the slider 400 has a non-sensing region where the relative position of the distal end of the endoscope 100 with respect to the distal end of the treatment tool 200 varies while the relative position of the endoscope-coupling part 420 with respect to the treatment tool-coupling part 422 varies between the first position and the second position, and a sensing region where the relative position of the distal end of the endoscope 100 with respect to the distal end of the treatment tool 200 does not vary with the relative position of the endoscope-coupling part 420 with respect to the treatment tool-coupling part 422 being the first position or the second position.

In the first embodiment of the processing of the control unit 150 serving as the switching means, the control unit 150 (switching means) activates the operation of the zooming means by the foot switch 156 in a case where the relative position of the endoscope-coupling part 420 with respect to the treatment tool-coupling part 422 has a shorter distance from the second position than a distance from the first position. Moreover, the control unit 150 deactivates the operation of the zooming means by the foot switch 156 in a case where the relative position of the endoscope-coupling part 420 with respect to the treatment tool-coupling part 422 has a shorter distance from the first position than a distance from the second position.

Figure 18:
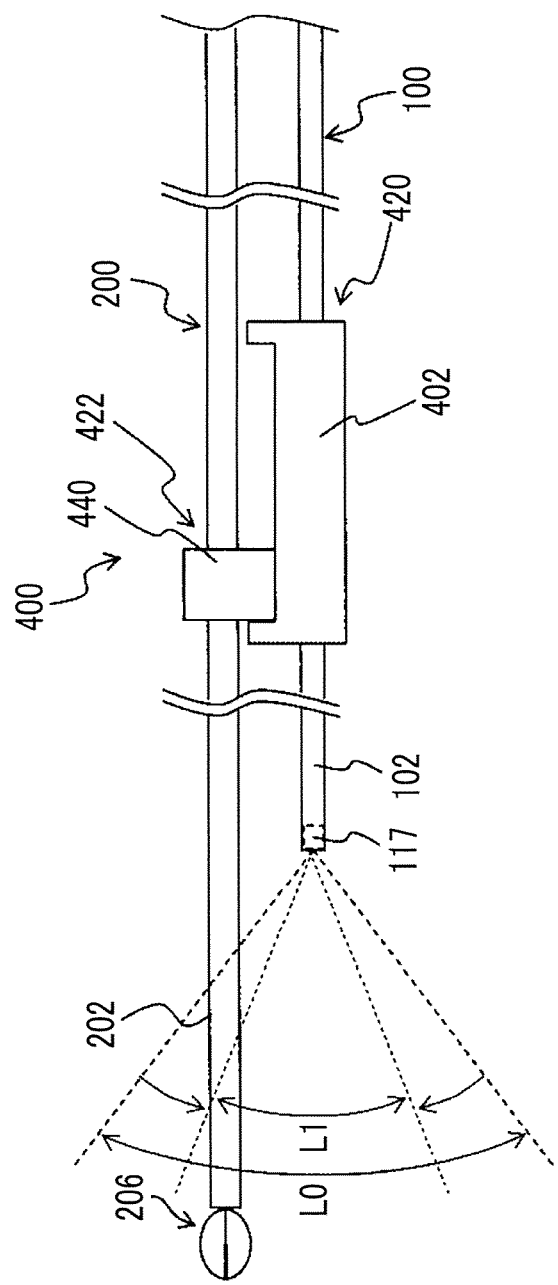
FIG. 18 is a view illustrating a state when the relative position of the endoscope-coupling part with respect to the treatment tool-coupling part is a second position.
Figure 19:
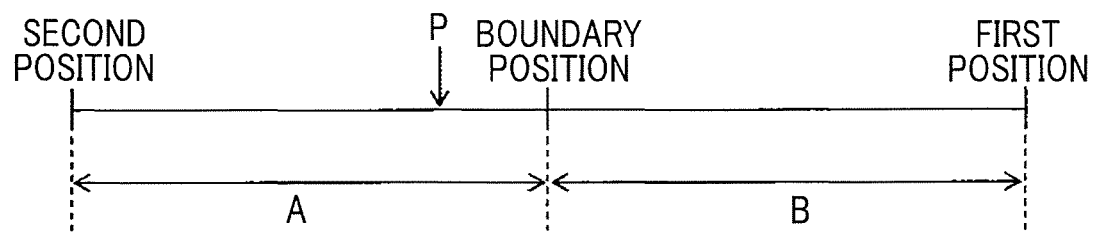
FIG. 19 is a view in which a current position of a sleeve with respect to a slider body is displayed on a horizontal axis.

That is, the position of the sleeve 440 with respect to the slider body 402 detected by the detecting means 160 when the relative position of the endoscope-coupling part 420 with respect to the treatment tool-coupling part 422 is the first position as illustrated in FIG. 17 is defined as the first position (the position when the sleeve 440 reaches the rear end of the movable range thereof with respect to the slider body 402), and the position of the sleeve 440 with respect to the slider body 402 detected by the detecting means 160 when the relative position of the endoscope-coupling part 420 with respect to the treatment tool-coupling part 422 is the second position as illustrated in FIG. 18 is defined as the second position (the position when the sleeve 440 reaches the front end of the movable range thereof with respect to the slider body 402). If a current position P of the sleeve 440 with respect to the slider body 402 detected by the detecting means 160 is displayed on a horizontal axis, the current position is displayed as illustrated in FIG. 19.

In this case, the control unit 150 activates the operation of the zooming means by the foot switch 156 when the current position P of the sleeve 440 detected by the detecting means 160 is located within a position range A closer to the second position side than a boundary position that is an intermediate position between the first position and the second position. On the other hand, when the current position P of the sleeve 440 detected by the detecting means 160 is located within a position range B closer to the first position side than the boundary position, the operation of the zooming means by a foot switch 156 is deactivated.

According to this, the operator can perform the following zooming operation.

First, as illustrated in (A) part of FIG. 13 or (A) part of FIG. 14, after the outer tube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the outer tube 300, and the endoscope insertion part 102 and the treatment tool insertion part 202 are mounted on the outer tube 300.

Then, if the operator moves the treatment tool insertion part 202 forward with his/her hand gripping the operating part 204 of the treatment tool 200, as illustrated in (B) part of FIG. 13 or (B) part of FIG. 14, the sleeve 440 moves forward with respect to the slider body 402, and the distal end of the endoscope 100 is separated from the distal end of the treatment tool 200. In this case, the current position P of the sleeve 440 with respect to the slider body 402 detected by the detecting means 160 becomes a position within the position range A in FIG. 19, and the operation of the zooming means by the foot switch 156 is activated.

Here, an observation visual field range L0 that is an image pickup range corresponding to an output image when the image processing unit 152 (zooming means) sets the zoom magnification factor of the endoscopic image as one time, that is, the observation visual field range L0 corresponding to an output image when the electronic zooming processing is not carried out is illustrated in FIGS. 17 and 18. As can be understood from these drawings, if the distal end of the endoscope 100 is separated from the distal end of the treatment tool 200 as illustrated in FIG. 18, the size of the image of the distal end site (treatment part 206) of the treatment tool 200 that appears in the output image becomes small.

Therefore, when the operator performs a depression operation of the zoom-in switch 156*a* of the foot switch 156 with his/her foot, an observation visual field range corresponding to the output image can be made small as illustrated in an observation visual field range L1 of FIG. 18 by increasing the zoom magnification factor of the output image. The image of the distal end site of the treatment tool 200 that appears in the output image can be zoomed in.

Accordingly, the image of the distal end site of the treatment tool 200 and a lesioned site therearound can be observed with the same size as that in a case where the distal end of the endoscope 100 is close to the distal end of the treatment tool 200.

Additionally, since the distal end of the endoscope 100 is apart from the distal end of the treatment tool 200, the zoom magnification factor is increased, and even if the lesioned site is zoomed in, the treatment tool 200 appears within the range the endoscopic image (output image). That is, if an attempt to fix the observation visual field range L0 from the state of FIG. 18 to zoom in the lesioned site, the state of FIG. 17 is brought about. However, in the state of FIG. 17, only the distal end of the treatment tool 200 appears in the range of the output image, and the entire treatment tool cannot be easily ascertained.

Therefore, the lesioned site can be zoomed in leaving the treatment tool 200 within the range of the output image by increasing the zoom magnification factor to change the observation visual field range while maintaining a positional relationship between the endoscope 100 and the treatment tool 200 in the state of FIG. 18.

Additionally, in a state illustrated in (A) part of FIG. 15 that is the state same as that of (A) part of FIG. 13 and (A) part of FIG. 14, even in a case where the operator passes the index finger of his/her right hand gripping the operating part 204 of the treatment tool 200 into the opening of any hooking part 132 of the forward and backward movement operating part 130, and moves his/her index finger backward to move the endoscope 100 backward, the slider body 402 moves backward with respect to the sleeve 440 as illustrated in (C) part of FIG. 15, and the distal end of the endoscope 100 is separated from the distal end of the treatment tool 200 as illustrated in FIG. 18. Then, the current position P of the sleeve 440 with respect to the slider body 402 detected by the detecting means 160 becomes a position within the position range A in FIG. 19, and the operation of the zooming means by the foot switch 156 is activated. In addition, the operation of moving the endoscope 100 backward is not limited to the operation method illustrated here.

In a case where the operator performs such a backward movement operation of the endoscope 100, it is considered that zoom-in of the range of the site to be observed that appears in the output image is intended. As illustrated in FIG. 18, in a case where the position of the sleeve 440 with respect to the slider body 402 reaches the second position (the front end of the movable range), a case where an attempt to further zoom in the range of the site to be observed that appears in the output image is made is considered.

Therefore, in such a case, when the operator performs a depression operation of the zoom-out switch 156*b* of the foot switch 156 with his/her foot, an observation visual field range corresponding to the output image can be made large by reducing the zoom magnification factor of the output image. The range of the site to be observed that appears in the output image can be zoomed in (the image of the site to be observed can be zoomed out).

On the other hand, in a case where the operator performs a backward movement operation of the endoscope 100, it is considered that a change in an angle at which the distal end site (treatment part 206) of the treatment tool 200 is imaged is intended. In this case, since the image of the site to be observed that appears in the output image also becomes small, a case where an attempt to zoom in the image of the site to be observed is made is considered. In such a case, when the an operator performs a depression operation of the zoom-in switch 156*a* of the foot switch 156 with his/her foot to increase the zoom magnification factor of the output image, the image of the site to be observed that appears in the output image can be zoomed in.

In a case where the operator moves the treatment tool 200 backward or in a case where the operator moves the endoscope 100 forward after the zoom magnification factor of the output image is changed as described above, the sleeve 440 moves backward with respect to the slider body 402. Then, the current position P of the sleeve 440 with respect to the slider body 402 detected by the detecting means 160 becomes a position within the position range B in FIG. 19, and the operation of the zooming means by the foot switch 156 is deactivated. This can prevent the operator from unintentionally operating the zooming means with the foot switch 156.

In addition, in a case where the operation of the zooming means by the foot switch 156 is deactivated, the zooming state (zoom magnification factor) till then may be maintained, or the zooming state may also be released such that the zoom magnification factor of the output image may be automatically returned to, for example, one time (a specified zoom magnification factor that is determined in advance). In this case, the time and efforts that are required for the operator to return the zoom magnification factor to the specified magnification factor can be reduced.

Next, if a second embodiment of the processing of the control unit 150 serving as the switching means is described, the control unit 150 (switching means) activates the operation of the zooming means by the foot switch 156 in a case where the relative position of the endoscope-coupling part 420 with respect to the treatment tool-coupling part 422 has a shorter distance from the first position than the distance from the second position. Moreover, the control unit 150 deactivates the operation of the zooming means by the foot switch 156 in a case where the relative position of the endoscope-coupling part 420 with respect to the treatment tool-coupling part 422 has a shorter distance from the second position than the distance from the first position.

That is, when the current position P of the sleeve 440 detected by the detecting means 160 is located within the position range B closer to the first position side than the boundary position as illustrated in FIG. 19, the control unit 150 activates the operation of the zooming means by a foot switch 156. On the other hand, when the current position P of the sleeve 440 detected by the detecting means 160 is located within the position range A closer to the second position side than the boundary position, the operation of the zooming means by a foot switch 156 is deactivated.

According to this, the operator can perform the following zooming operation.

In the state illustrated in (A) part of FIG. 13 or (A) part of FIG. 14, if the operator moves the treatment tool insertion part 202 backward with his/her hand gripping the operating part 204 of the treatment tool 200, as illustrated in (C) part of FIG. 13 or (C) part of FIG. 14, the sleeve 440 moves backward with respect to the slider body 402, and the distal end of the endoscope 100 approaches the distal end of the treatment tool 200. In this case, the current position P of the sleeve 440 with respect to the slider body 402 detected by the detecting means 160 becomes a position within the position range B in FIG. 19, and the operation of the zooming means by the foot switch 156 is activated.

Then, if the distal end of the endoscope 100 approaches the distal end of the treatment tool 200 as illustrated in FIG. 17, the size of the image of the distal end site (treatment part 206) of the treatment tool 200 that appears in the output image becomes large.

Therefore, when the operator performs a depression operation of the zoom-in switch 156*a* of the foot switch 156 with his/her foot, an observation visual field range corresponding to the output image can be made small as illustrated in the observation visual field range L1 of FIG. 17 by increasing the zoom magnification factor of the output image. The image of the distal end site of the treatment tool 200 or the lesioned site that appears in the output image can be zoomed in.

According to this, when an attempt to zoom in the image of the site to be observed that appears in the output image is made, the image is zoomed in by the operation of the treatment tool 200. However, the lesioned site or the distal end site (treatment part 206) of the treatment tool 200 can be observed in more detail by using the zooming means together.

Additionally, another zooming operation form when the treatment tool insertion part 202 is moved backward and the distal end of the endoscope 100 is brought close to the distal end of the treatment tool 200 close is also possible. For example, it is also considered that, when the operator performs a depression operation of the zoom-out switch 156*b* of the foot switch 156 with his/her foot, an observation visual field range corresponding to the output image can be made large as illustrated in the observation visual field range L2 of FIG. 21 by reducing the zoom magnification factor of the output image, and the image of the distal end site of the treatment tool 200 or the lesioned site that appears in the output image is zoomed out.

Accordingly, an image of the distal end site of the treatment tool 200 and the lesioned site therearound can be observed with the same size as that in a case where the distal end of the endoscope 100 is separated from the distal end of the treatment tool 200.

Additionally, for example, in the state illustrated in (A) part of FIG. 15 that is the state same as that of (A) part of FIG. 13 and (A) part of FIG. 14, the operator passes the index finger of his/her right hand gripping the operating part 204 of the treatment tool 200 into the opening of any hooking part 132 of the forward and backward movement operating part 130, and moves his/her index finger forward to move the endoscope 100 forward. Even in this case, the slider body 402 moves forward with respect to the sleeve 440 as illustrated in (B) part of FIG. 15, and the distal end of the endoscope 100 approaches the distal end of the treatment tool 200 as illustrated in FIG. 17. Then, the current position P of the sleeve 440 with respect to the slider body 402 detected by the detecting means 160 becomes a position within the position range B in FIG. 19, and the operation of the zooming means by the foot switch 156 is activated. In addition, the operation of moving the endoscope 100 forward is not limited to the operation method illustrated here.

In a case where the operator performs such a forward movement operation of the endoscope 100, it is considered that zoom-in (zoom-out of the range of the site to be observed) of the image of the site to be observed that appears in the output image is intended. As illustrated in FIG. 17, in a case where the position of the sleeve 440 with respect to the slider body 402 reaches the first position (the rear end of the movable range), a case where an attempt to further zoom in the image of the site to be observed that appears in the output image is made is considered.

Therefore, in such a case, when the operator performs a depression operation of the zoom-in switch 156a of the foot switch 156 with his/her foot, an observation visual field range corresponding to the output image can be made small by increasing the zoom magnification factor of the output image. The image of the site to be observed that appears in the output image can be zoomed in (the range of the site to be observed can be reduced).

On the other hand, in a case where the operator performs a forward movement operation of the endoscope 100, it is considered that a change in an angle at which the distal end site (treatment part 206) of the treatment tool 200 is imaged is intended. In this case, since the range of the site to be observed that appears in the output image also becomes small, a case where an attempt to zoom in the range of the site to be observed is made is considered. In such a case, when the an operator performs a depression operation of the zoom-out switch 156b of the foot switch 156 with his/her foot to reduce the zoom magnification factor of the output image, the range of the site to be observed that appears in the output image can be zoomed in.

In a case where the operator moves the treatment tool insertion part 202 forward or in a case where the operator moves the endoscope 100 backward after the zoom magnification factor of the output image is changed as described above, the sleeve 440 moves forward with respect to the slider body 402. Then, the current position P of the sleeve 440 with respect to the slider body 402 detected by the detecting means 160 becomes a position within the position range A in FIG. 19, and the operation of the zooming means by the foot switch 156 is deactivated.

In addition, in a case where the operation of the zooming means by the foot switch 156 is deactivated, similar to the first embodiment, the zooming state (zoom magnification factor) till then may be maintained, or the zooming state may also be released such that the zoom magnification factor of the output image may be automatically returned to, for example, one time (a specified zoom magnification factor that is determined in advance). In this case, the time and efforts that are required for the operator to return the zoom magnification factor to the specified magnification factor can be reduced.

As described above, in any of the first embodiment and the second embodiment of the processing of the control unit 150 serving as the switching means, as illustrated in FIG. 19, the control unit 150 (switching means) is adapted to switch between the activation and deactivation of the operation of the zooming means by the zoom operating means (foot switch 156) with the intermediate position between the first position and the second position being the boundary position. However, the boundary position can be set to arbitrary positions. It should be noted herein that it is desirable that the boundary position in the first embodiment is set a position closer to the second position than the intermediate position of the first position and the second position, and it is desirable that the boundary position in the second embodiment is set to a position closer to the first position than the intermediate position between the first position and the second position.

Figure 20:
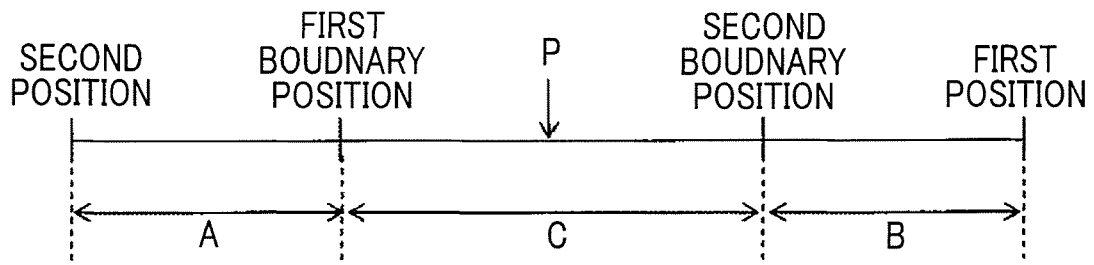
FIG. 20 is an explanatory view used for description of another form regarding the processing of a control unit serving as switching means, and a view in which a current position of the sleeve with respect to the slider body is displayed on the horizontal axis.

Additionally, it is also possible to adopt a form in which the first embodiment and the second embodiment are combined together regarding the processing of the control unit 150 serving as the switching means. That is, as illustrated in FIG. 20, a first boundary position and a second boundary position are set between the first position and the second position. It should be noted herein that the first boundary position is set closer to the second position side than the second boundary position.

In a case where the current position P of the sleeve 440 detected by the detecting means 160 is located within the position range A closer to the second position than the first boundary position, and in a case where the current position P is located within the position range B closer to the first position than the second boundary position, the operation of the zooming means by the foot switch 156 is activated. On the other hand, in a case where the current position P of the sleeve 440 is located within a position range C between the first boundary position and the second boundary position, the operation of the zooming means by the foot switch 156 is deactivated.

Additionally, in the zooming system in the above surgical apparatus for an endoscope 10, the zoom magnification factor of the endoscopic image (output image) is changed by the electronic zooming processing in the image processing unit 152 so as to perform the zoom-in or zoom-out of the image and the range of the site to be observed that appears in the output image. However, the same processing may be performed not by the electronic zooming but by optical zooming.

That is, in the observation part of the endoscope 100, a zoom optical system in which the zoom magnification factor (focal distance) can be changed by driving of an actuator (drive means) is mounted as zooming means of the observation optical system that forms an optical image on the light-receiving surface of the image pickup element 117. Additionally, the zoom magnification factor of the zoom optical system is configured to be changed by driving the actuator (drive means) with a control signal from the control unit 150.

Also, the control unit 150 performs the change of the zoom magnification factor performed with respect to the image processing unit 152 in the above embodiment, and the switching between the activation and deactivation of the operation of the zooming means by the foot switch 156 is performed with respect to the zoom optical system. Accordingly, zoom-in, zoom-out, or the like of the image of the lesioned site in the output image can be performed by the optical zooming, similar to the above embodiment.

EXPLANATION OF REFERENCES

10: surgical apparatus for endoscope
100: endoscope
102: endoscope insertion part
104: cable part
108: processor device
110: light source device
112: monitor
116: observation window
118: illumination window
130: forward and backward movement operating part
150: control unit
152: image processing unit
154: display control unit
156: foot switch
160: detecting means
160a: resistor
160b: slider
200: treatment tool
202: treatment tool insertion part
204: operating part
206: treatment part
300: outer tube
300a: reference axis
306: endoscope insertion passage
306a: endoscope insertion axis
308: treatment tool insertion passage
308a: treatment tool insertion axis
310: first base end opening
312: first distal end opening
314: second base end opening
316: second distal end opening
320: long tubular outer tube body
340: base end cap
360: distal end cap
400: slider
402: slider body
420: endoscope-coupling part
422: treatment tool-coupling part
440: sleeve
444: sleeve body
446: pressure-contact member
500: exterior tube

What is claimed is:

1. A surgical apparatus for an endoscope comprising:
an endoscope having an image pickup element disposed at a distal end thereof;
a treatment tool having a treatment part at a distal end thereof;
an outer tube that passes through a body wall and is inserted into a body cavity to guide the endoscope and the treatment tool into the body cavity; and
a control device connected to the endoscope,
wherein the outer tube includes
an outer tube body having a distal end, a base end, and a longitudinal axis,
a first distal end opening and a second distal end opening provided at the distal end of the outer tube body,
a first base end opening and a second base end opening provided at the base end of the outer tube body,
an endoscope insertion passage that is provided along the longitudinal axis of the outer tube body, allows the first distal end opening and the first base end opening to communicate with each other therethrough, and allows the endoscope to be inserted therethrough so as to be movable forward and backward,
a treatment tool insertion passage that is provided along the longitudinal axis of the outer tube body, allows the second distal end opening and the second base end opening to communicate with each other therethrough, and allows the treatment tool to be inserted therethrough so as to be movable forward and backward, and
an interlocking member that has an endoscope-coupling part coupled to the endoscope inserted through the endoscope insertion passage, and a treatment tool-coupling part coupled to the treatment tool inserted through the treatment tool insertion passage and is movable forward and backward inside the outer tube body,
wherein, a relative position of the endoscope-coupling part with respect to the treatment tool-coupling part when the distal end of the endoscope approaches the distal end of the treatment tool most in a longitudinal axis direction of the outer tube body is defined as a first position, and a relative position of the endoscope-coupling part with respect to the treatment tool-coupling part when the distal end of the endoscope is separated from the distal end of the treatment tool most in the longitudinal axis direction of the outer tube body is defined as a second position, the interlocking member has a non-sensing region where the relative position of the distal end of the endoscope with respect to the distal end of the treatment tool varies while the relative position of the endoscope-coupling part with respect to the treatment tool-coupling part varies between the first position and the second position, and a sensing region where the relative position of the distal end of the endoscope with respect to the distal end of the treatment tool does not vary while the relative position of the endoscope-coupling part with respect to the treatment tool-coupling part is the first position or the second position, and
wherein the endoscope or the control device includes
a zooming unit configured to change a zoom magnification factor of an endoscopic image picked up by the image pickup element, and
a zoom operating unit which is provided in the endoscope or the control device and is configured to operate the zooming unit based on a user input,
the surgical apparatus for an endoscope further comprising:
a detecting unit configured to detect the relative position of the distal end of the endoscope with respect to the distal end of the treatment tool in the longitudinal axis direction of the outer tube body; and
a switching unit configured to switch between activation and deactivation of the operation of the zooming unit by the zoom operating unit, on the basis of a detection result of the detecting unit;
wherein the detecting unit detects the relative position of the endoscope-coupling part with respect to the treatment tool-coupling part, thereby detecting the relative position of the distal end of the endoscope with respect to the distal end of the treatment tool.

2. The surgical apparatus for an endoscope according to claim 1,
wherein the switching unit activates the operation of the zooming unit by the zoom operating unit in a case where the relative position of the endoscope-coupling part with respect to the treatment tool-coupling part has a shorter distance from the second position than a distance from the first position, and deactivates the operation of the zooming unit by the zoom operating unit in a case where the relative position of the endoscope-coupling part with respect to the treatment tool-coupling part has a shorter distance from the first position than a distance from the second position.

3. The surgical apparatus for an endoscope according to claim 1,
wherein the switching unit activates the operation of the zooming unit by the zoom operating unit in a case where the relative position of the endoscope-coupling part with respect to the treatment tool-coupling part has a shorter distance from the first position than a distance from the second position, and deactivates the operation of the zooming unit by the zoom operating unit in a case where the relative position of the endoscope-coupling part with respect to the treatment tool-coupling part has a shorter distance from the second position than a distance from the first position.

4. The surgical apparatus for an endoscope according to claim 1,
wherein the zooming unit changes the zoom magnification factor through at least one of optical zooming or electronic zooming.

5. The surgical apparatus for an endoscope according to claim 1,
wherein the zoom operating unit has a first operation switch that zooms in the endoscopic image, and a second operation switch that zooms out the endoscopic image.

6. The surgical apparatus for an endoscope according to claim 5,
wherein the zooming unit continuously changes the zoom magnification factor while the first operation switch or the second operation switch is continuously operated.

7. The surgical apparatus for an endoscope according to claim 1,
wherein the zoom operating unit is a foot switch.

* * * * *